United States Patent
Monassevitch et al.

(10) Patent No.: US 7,094,247 B2
(45) Date of Patent: *Aug. 22, 2006

(54) INTUSSUSCEPTION AND ANASTOMOSIS APPARATUS

(75) Inventors: Leonid Monassevitch, Givat Olga (IL); Benjamin Spenser, Caesarea (IL); Michael Arad, Tel-Aviv (IL); Ronen Ne'eman, Haifa (IL)

(73) Assignee: NiTi Medical Technologies Ltd., Netanya (IL)

( * ) Notice: Subject to any disclaimer, the term of this patent is extended or adjusted under 35 U.S.C. 154(b) by 738 days.

This patent is subject to a terminal disclaimer.

(21) Appl. No.: 10/237,505

(22) Filed: Sep. 9, 2002

(65) Prior Publication Data

US 2004/0015179 A1 Jan. 22, 2004

(30) Foreign Application Priority Data

Jul. 22, 2002 (IL) .................................. 150853

(51) Int. Cl.
*A61B 17/08* (2006.01)
(52) U.S. Cl. ..................................... 606/153; 606/151
(58) Field of Classification Search ................ 606/151, 606/153, 156, 213, 215, 185; 623/1.1, 1.11
See application file for complete search history.

(56) References Cited

U.S. PATENT DOCUMENTS

| 5,197,648 | A | 3/1993 | Gingold |
| 5,312,024 | A | 5/1994 | Grant et al. |
| 5,344,059 | A | 9/1994 | Green et al. |
| 5,411,508 | A | 5/1995 | Bessler et al. |
| 5,639,008 | A | 6/1997 | Gallagher et al. |
| 6,117,148 | A * | 9/2000 | Ravo et al. ................. 606/153 |
| 6,884,250 | B1 * | 4/2005 | Monassevitch et al. ..... 606/153 |

* cited by examiner

*Primary Examiner*—Julian W. Woo
(74) *Attorney, Agent, or Firm*—Pearne & Gordon LLP

(57) ABSTRACT

Apparatus for intratubular intussusception and anastomosis of a hollow organ portion including a cylindrical enclosure, coaxial intratubular intussusception device, for intussusception and clamping means. The apparatus also includes an intratubular anastomosis apparatus for joining organ portions after intussusception thereof with an anastomosis ring and crimping support element. The ring is formed of a shape memory alloy wire, for crimping adjacent organ portions against the crimping support element so as to cause anastomosis therebetween. The ring assumes a plastic or malleable state, at a lower temperature and an elastic state at a higher temperature. The apparatus further includes the crimping support element for intratubular insertion so as to provide a support for crimping the organ portions against the support element. The apparatus additionally includes a surgical excising means, for excising an intussuscepted organ portion, after crimping adjacent intussuscepted organ walls against the crimping support element with the anastomosis ring.

16 Claims, 34 Drawing Sheets

INTUSSUSCEPTION AND ANASTOMOSIS APPARATUS

FIELD OF THE INVENTION

The present invention relates, generally to intussusception and anastomosis and, more specifically, to intussusception and anastomosis apparatus.

GLOSSARY

Intussusception: a drawing in of something from without, especially, the slipping of a length of intestine into an adjacent portion.

Anastomosis: the union of parts or branches (as of streams, blood vessels, or leaf veins) so as to intercommunicate therebetween.

Proximal: Situated close to the user.

Distal: Situated away or distant from the user (relative to Proximal)

BACKGROUND OF THE INVENTION

It is known in the art to provide an excision of a segment of diseased colon or intestine as a result, for example, of a perforation, bleeding, inflammation, or tumor and to provide an anastomosis of the cut end portions. This can be conducted by opening the peritoneal cavity or laparoscopically. However, there are two significant problems associated with these procedure.

The integrity of the anastomosis must be sound so that there is no risk of the anastomosis rupturing or leaking into the peritoneal cavity, causing contamination of the clean interior of the peritoneal cavity. Further, opening the bowel and exposing the clean peritoneal cavity to contamination increases the risk of postoperative complications. There have been a number of improvements in the anastomosis procedure over the past decade.

Reference is made to U.S. Pat. No. 5,197,648 to Gingold on Mar. 30, 1993 entitled "Surgical stapling apparatus." There is disclosed an improved circular anastomosis surgical stapling instrument for joining hollow tubular organs. The instrument includes a staple-carrying assembly at its distal end, a centered longitudinally extensible and retractable main shaft centered in the body, and an anvil opposed to the staple-carrying assembly. In a preferred form, the end of the main shaft is provided with a plurality of radially extendable arms positioned to overlie the main shaft having spring hinges biasing them radially outwardly away from the main shaft. The instrument also has a second shaft segment in the hollow of the main shaft, which has a conical pointed unit at its distal end.

Reference is also made to U.S. Pat. No. 5,312,024 to Grant, et al. on May 17, 1994 entitled "Surgical anastomosis stapling instrument with flexible support shaft and anvil adjusting mechanism." There is disclosed a stapling instrument for circular anastomosis stapling. The instrument includes a stapling head flexibly mounted by a support shaft to an actuator handle. The support shaft is radially flexible and suitable for insertion into a patient. The flexible support shaft includes a dual coil structure, to be self-supporting in any curved configuration and to resist deflection upon insertion into the patient during actuation of the stapler. The stapling head includes a driver assembly, which is operable to separate staple forming and tissue cutting actions. The actuator handle includes a staple actuator and a cam follower assembly, to facilitate the operation of the instrument by a surgeon. The actuator handle includes a thumb wheel for opening and closing the anvil and an adjusting knob for adjusting the anvil gap. There is also provided a control lever for pivoting the stapling head relative to the flexible support shaft.

Reference is further made to U.S. Pat. No. 5,344,059 to Green, et al. on Sep. 6, 1994 entitled "Surgical apparatus and anvil delivery system therefore." There is disclosed a detachable anvil assembly for use with a circular anastomosis apparatus for tubular organs. This includes an anvil rod with an anvil head mounted on the distal end thereof. The distal end portion is adapted to pivot by about ninety degrees relative to the axis of the rod. A delivery? facilitates delivery of the anvil assembly to the operative site. The pivoting feature of the distal end reduces the transverse profile of the assembly, consequently facilitating introduction and advancement of the anvil assembly into the organ.

Referring, additionally, to U.S. Pat. No. 5,411,508 to Bessler, et al. on May 2, 1995 entitled "Gastrointestinal approximating and tissue attaching device," there is disclosed a steerable intestinal endoscopic stapler. The stapler comprises a circular anvil with a circular stapling anvil surface and a trimming surface, disposed radially inwardly of the stapling surface. A circular stapler drives staples in an array corresponding to the anvil surface and a circular cutting blade operates corresponding to the cutting block. A scope in the hand piece, optically connected to a lens in the head assembly, is provided for viewing beyond the head assembly. A steering arrangement is provided for steering the head assembly. An activator at the hand piece is for driving staples toward the anvil and for driving the cutting blade toward the cutting block. Tubular tissue ends are joined by staples and excess tissue is trimmed off with the blade.

In addition, reference is made to U.S. Pat. No. 5,639,008 to Gallagher, et al. on Jun. 17, 1997 entitled "Anvil for circular stapler." There is disclosed an anvil for a fastening instrument. The anvil pivots relative to a shaft to facilitate movement of the anvil and instrument. The anvil also has an improved surface for severing tissue and a sloped surface for guiding a knife during use.

In order to avoid opening the bowel and exposing the clean peritoneal cavity, intussusception of the colon or intestine enables the excision to be conducted extra corporeally, that is, outside the body cavity, preventing contamination of the body cavity. There has been a development recently whereby the intussusception, anastomosis and resection of the intussuscepted segment is facilitated.

Reference is made to U.S. Pat. No. 6,117,148 to Ravo, et al. on Sep. 12, 2000 entitled "Intraluminal anastomotic device." There is disclosed a bowel intussusception, anastomosis and severing mechanism for the resected bowel. The device enables these procedures, without exposing the contaminated intraluminal content to the clean abdominal or thoracic cavities. By tying the bowel to a post, which is withdrawn, intussusception is accomplished. Thereafter, anastomosis by stapling and finally intraluminal resection is carried out.

Each of the foregoing inventions utilizes stapling for causing anastomosis of the portions of bowel or intestine to be joined. It would be advantageous to utilize a procedure and apparatus that did not rely on applying a plurality of staples or other connecting devices, which, of necessity, remain in the bowel and which, despite the utmost care by the surgeon, may leak or rupture. There are also advantages to further facilitating and improving the intussusception procedure.

SUMMARY OF THE INVENTION

The present invention aims to provide an apparatus for intratubular removal of a diseased portion of an hollow organ, which has, for example, a tumor, inflammation, ulcer or other trauma, without exposing the peritoneal cavity to contaminants generally present within such hollow organs. The apparatus includes elements for intussusception, anastomosis and excision. The diseased organ portion is removed, and the severed ends crimped together using an anastomosis ring formed of a shape memory alloy and a crimping support element, without exposure of the peritoneal cavity to, for example, bowel contaminants. Initial patency of the gastrointestinal tract is immediately created. The anastomosis ring and crimping support element subsequently become detached from the organ when anastomosis is complete and are passed through the bowel.

According to a preferred embodiment of the present invention, there is provided an intratubular anastomosis apparatus for joining organ wall portions of a hollow organ after intussusception. The apparatus includes an anastomosis ring, including a length of a wire formed of a shape memory alloy defining a closed generally circular shape, having a central opening, and having overlapping end portions, the anastomosis ring for crimping adjacent intussuscepted organ wall portions against a crimping support element so as to cause anastomosis therebetween. The anastomosis ring and the shape memory alloy assume a plastic or maleable state, when at a first, lower temperature and an elastic state, when reaching at least a second, higher temperature, thereby enabling the anastomosis ring to retain a preselected configuration at the first, lower temperature, and an elastic crimping configuration upon reverting to the second, higher temperature. The apparatus also includes the crimping support element for intratubular insertion so as to provide a support for crimping the organ wall portions against the support element. The crimping support element has a generally cylindrical side-wall; proximal and distal end walls formed generally transversely to the side-wall, thereby to define therewith the crimping support element, a generally axial aperture for providing flow communication therethrough, and attachment means for operationally engaging the crimping support element to a crimping applicator member so as to position the crimping support element adjacent to the anastomosis ring for facilitating crimping of preselected wall portions of a hollow organ therebetween.

Also in accordance with a preferred embodiment of the present invention there is provided apparatus for intratubular intussusception and anastomosis of a preselected wall portion of a hollow organ. The apparatus includes a generally cylindrical enclosure member having a proximal and a distal end; an intratubular intussusception device, generally coaxially disposed within the enclosure member, for intussusception of a preselected hollow organ portion to be excised from the hollow organ. The intussusception device includes clamping means disposed at the distal end, and activating means, operationally connected to the clamping means, disposed at the proximal end. The apparatus further includes an intratubular anastomosis apparatus disposed within the enclosure member for joining the wall portions of the hollow organ after intussusception. The anastomosis apparatus includes an anastomosis ring, including a length of a wire formed of a shape memory alloy defining a closed generally circular shape, having a central opening, and having overlapping end portions, the anastomosis ring for crimping adjacent intussuscepted organ wall portions against a crimping support element so as to cause anastomosis therebetween. The anastomosis ring and the shape memory alloy assumes a plastic state, when at a first, lower temperature and an elastic state, when reaching at least a second, higher temperature. This enables the anastomosis ring to retain a preselected configuration at the first, lower temperature, and an elastic crimping configuration upon reverting to the second, higher temperature. The anastomosis apparatus additionally includes the crimping support element for intratubular insertion so as to provide a support for crimping the organ wall portions against the support element. The crimping support element has a generally cylindrical side-wall, proximal and distal end walls arranged generally transversely to the side-wall, thereby to define therewith the crimping support element, a generally axial aperture for providing flow communication therethrough, and attachment means for operationally engaging the crimping support element to a crimping support element applicator member so as to position the crimping support element adjacent to the anastomosis ring. The apparatus further includes a surgical excising means, for excising preselected intussuscepted hollow organ portion, the excising means operatively associated with the intratubular anastomosis apparatus, selectably operable, after crimping adjacent intussuscepted organ walls against the crimping support element with the anastomosis ring.

According to a first embodiment of the present invention, the intratubular anastomosis apparatus, includes the length of wire which is formed having a cross-sectional shape substantially circular and elliptical, thereby to control pressure applied to tissue compressed between the anastomosis ring and the crimping support element.

According to a second embodiment of the present invention, the anastomosis ring is a contracting or an expanding anastomosis ring at the second higher temperature.

According to a third embodiment of the present invention, the crimping support member has a circumferential recess formed in an outer or an inner surface thereof for facilitating retaining the contracting anastomosis ring in a predetermined position therein.

According to a fourth embodiment of the present invention, the intratubular anastomosis apparatus in which the crimping support member is configured as a crimping support helix includes one or more coils formed of shape memory alloy such that the crimping support helix is an expanding support helix at the second higher temperature.

According to a fifth embodiment of the present invention, the apparatus for intratubular intussusception and anastomosis has a clamping means which includes a coaxial pair of jaw elements having a generally disc-like configuration operatively disposed to move relative to each other and to the apparatus.

According to a sixth embodiment of the present invention, the apparatus for intratubular intussusception and anastomosis has activating means, operationally connected to the clamping means, which is remotely disposed therefrom.

According to a seventh embodiment of the present invention, the apparatus for intratubular intussusception and anastomosis has surgical excising means which includes a generally cylindrical cutting blade member operative axially.

According to an eighth embodiment of the present invention, the apparatus for intratubular intussusception and anastomosis has surgical excising means operatively associated with an excising controller remotely disposed therefrom.

According to a ninth embodiment of the present invention, the apparatus for intratubular intussusception and anastomosis includes an optical device, the optical device affixed to the apparatus, for permitting viewing of the organ being intussuscepted and anastomosed.

Furthermore, there is provided a method for intratubular intussusception and anastomosis of a hollow organ wall portion. The method includes steps of inserting a distal end portion of an apparatus for intratubular intussusception and anastomosis a preselected distance into an hollow organ; clamping a preselected portion of the hollow organ utilizing a clamping means of the intussusception and anastomosis apparatus; intussuscepting the preselected organ portion by withdrawing the clamping means a preselected distance into an enclosure member; disengaging an anastomosis ring from an anastomosis ring applicator member so as to crimp the intussuscepted organ portion against a crimping support element; and excising the intussuscepted organ portion.

According to a tenth embodiment of the present invention, the method step of inserting includes a step of demountably engaging the anastomosis ring formed of a shape memory alloy to the anastomosis ring applicator member. According to a variation of the tenth embodiment of the present invention the method step of demountably engaging includes a step of cooling the anastomosis ring below a first transition temperature so as to assume a plastic state thereof.

According to an eleventh embodiment of the present invention, the method step of clamping a preselected portion of the hollow organ includes a step of drawing a substantially middle portion of the preselected organ portion within the clamping means.

According to a twelfth embodiment of the present invention, the method, in which the preselected wall portion of a hollow organ has been subject to prolapse, includes the method steps of inserting a distal end portion of an apparatus for intratubular intussusception and anastomosis a preselected distance into an hollow organ so as to juxtapose a crimping support element and an anastomosis ring to the prolapsed organ portion; disengaging the anastomosis ring from an anastomosis ring applicator member so as to crimp the intussuscepted organ portion against the crimping support element; and excising the intussuscepted organ portion.

According to a thirteenth embodiment of the present invention, the method, in which the preselected wall portion of a hollow organ has been subject to surgical excision, includes the method steps of inserting a distal end portion of an apparatus for intratubular intussusception and anastomosis into an hollow organ to the surgically excised wall portion of a hollow organ; clamping of surgically excised bowel portions prior to anastomosis; intussuscepting the preselected organ portions by withdrawing the clamping means a preselected distance into an enclosure member; disengaging an anastomosis ring from an anastomosis ring applicator member so as to crimp the intussuscepted organ portion against a crimping support element; and excising the intussuscepted organ portion.

BRIEF DESCRIPTION OF THE DRAWINGS

The present invention will be more fully understood and its features and advantages will become apparent to those skilled in the art by reference to the ensuing description, taken in conjunction with the accompanying drawings, in which.

DETAILED DESCRIPTION OF THE INVENTION

The incidence of tumors, ulcers, inflammation and other traumas in the lower large intestine and in other sections of the intestinal tract is significantly high. In order to excise a diseased section of bowel represents a risk of causing contamination to the peritoneal cavity by the discharge from the exposed bowel interior. Also, joining the bowel portions after excising a section of bowel results in the risk of leakage or rupture of the join.

The present invention seeks to provide a solution to both problems by providing apparatus for an improved excision procedure and an improved joining technique. The removal of a troublesome portion of bowel is carried out by intratubular intussusception of that portion. Joining or anastomosis is then accomplished using an intratubular anastomosis apparatus concurrently with the intussusception of the bowel. The preferred fastening apparatus includes an anastomosis ring formed from a shape memory alloy in conjunction with a crimping support element, which become detached from the site when anastomosis is complete. In addition, the preferred fastening apparatus may also be used to achieve anastomosis following conventional or laproscopic excision of a diseased intestinal portion.

Figure 1A:
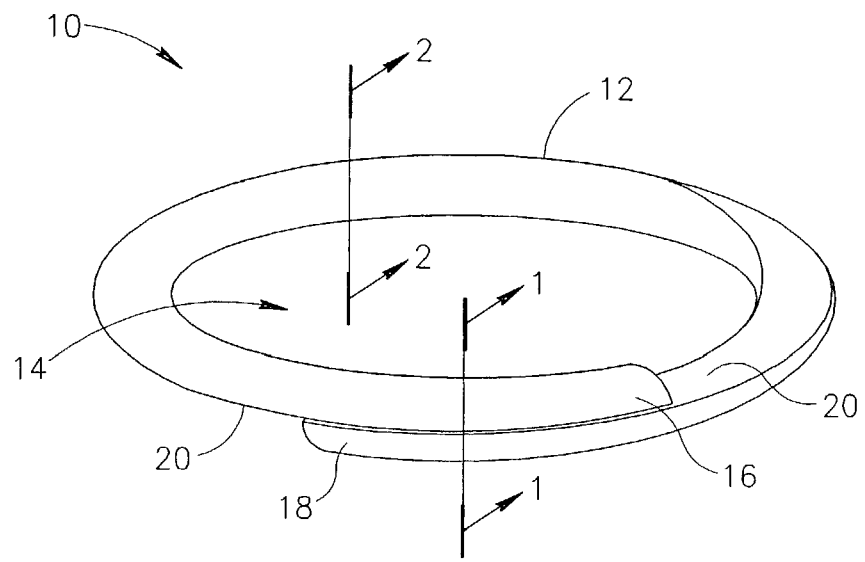
FIG. 1A illustrates a perspective view of an anastomosis ring.

With reference to FIGS. 1A–1D, there is seen, in accordance with a preferred embodiment of the present invention, in FIG. 1A an anastomosis ring generally referenced 10, which is configured from a length of shape memory alloy wire 12 as a closed generally circular shaped ring, having a central opening referenced 14, a predetermined wire thickness and overlapping end portions referenced 16 and 18.

Figure 1B:
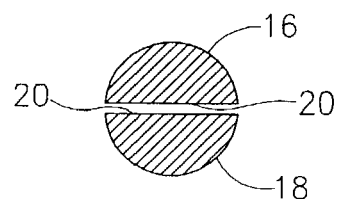
FIG. 1B illustrates a cross-sectional view of overlapping ends of an anastomosis ring as illustrated in FIG. 1A.

In FIG. 1B there is seen a cross-sectional view of overlapping end portions 16 and 18 of anastomosis ring 10 as taken along line 1—1 (FIG. 1A). Each of end portions 16 and 18 has a flat contact surface referenced 20 formed thereon so as to provide a similar cross-sectional profile at overlapping portions 16 and 18 as wire 12.

Figure 1C:
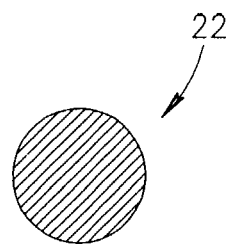
FIGS. 1C and 1D illustrate cross-sectional views of an anastomosis ring as illustrated in FIG. 1A, in accordance with alternative embodiments of the present invention.
Figure 1D:
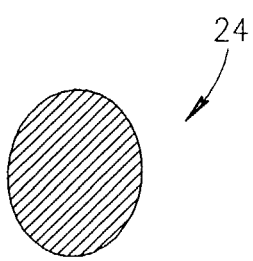

In order to control the pressure on the tissue walls at the point of contact with anastomosis ring 10, the cross-section of the wire forming ring 10 may be varied, in accordance with alternative embodiments of the present invention. In FIGS. 1C and 1D there are seen cross-sectional views, which are non-limiting examples only, of alternative profiles taken along line 2—2 of surgical clip 10 (FIG. 1A). In FIG. 1C there is seen a generally circular cross-sectional profile referenced 22. According to an alternative embodiment of the present invention, there is seen in FIG. 1D an elliptical profile referenced 24.

Figure 18:
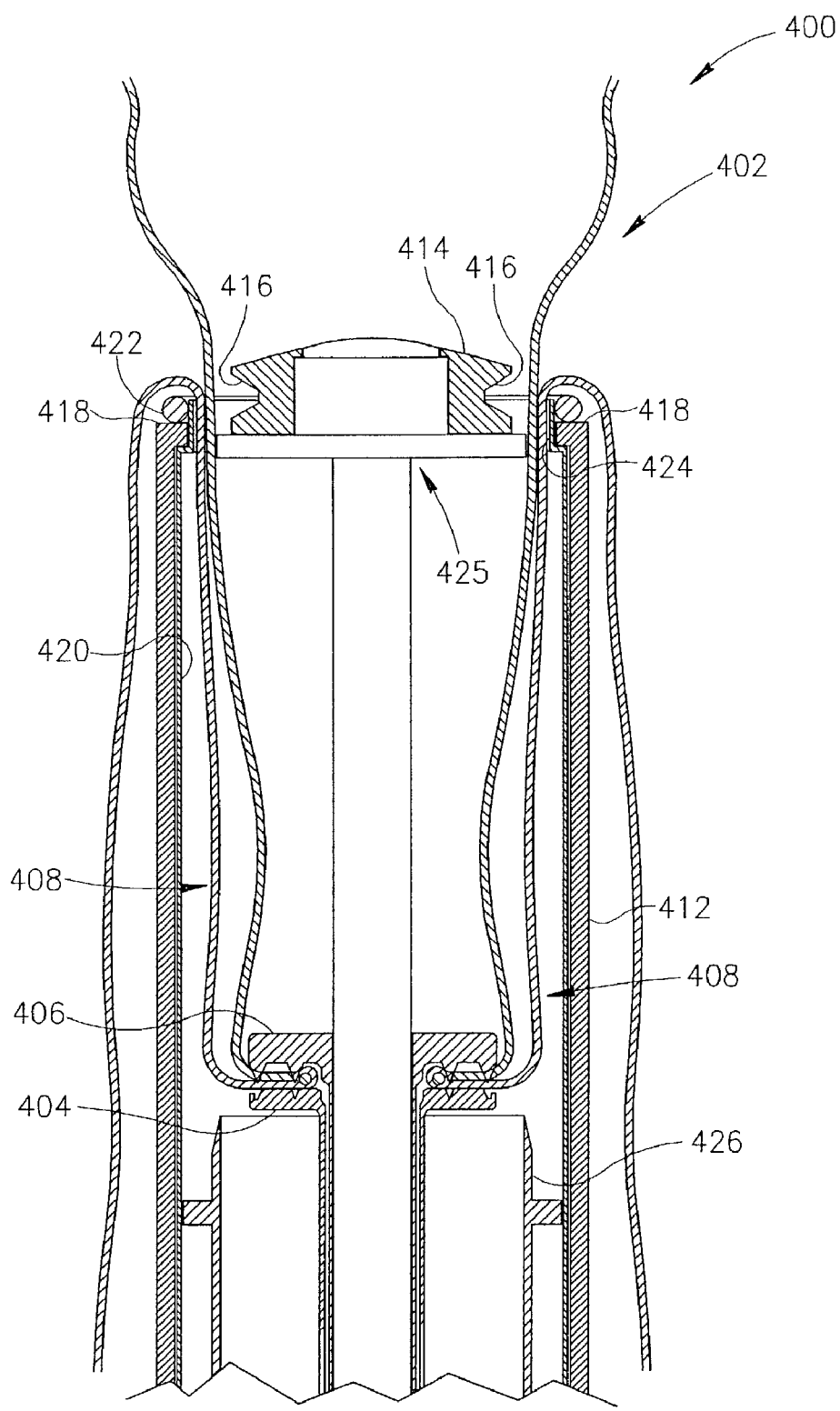
FIG. 18 illustrates a cross-sectional view of an intussuscepted bowel with a crimping support element positioned for crimping.

The shape memory alloy anastomosis ring 10 assumes a plastic or malleable state, when cooled to or below a first, lower temperature and an elastic state, when reaching and exceeding a second, higher temperature. This cooling enables anastomosis ring 10 to retain a malleable configuration at the first, lower temperature. Once the temperature of ring 10 has risen above the transition temperature, ring 10 returns fully to an elastic phase, and, as seen in FIG. 18 as referred to hereinbelow, ring 10 contracts and presses against and remains positioned on anastomosis ring applicator 420 in recess 424.

Figure 2A:
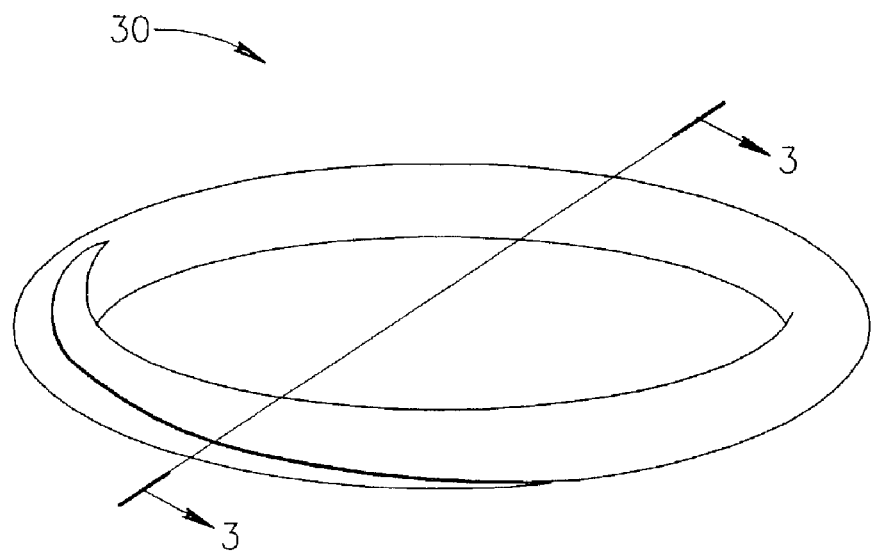
FIG. 2A illustrates a perspective view of an anastomosis ring having a constant circular cross-sectional area.
Figure 2B:
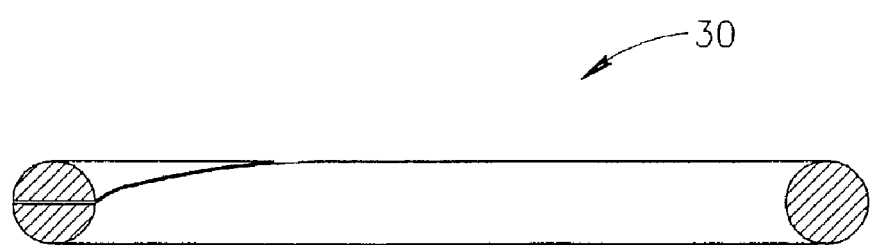
FIG. 2B illustrates a cross-sectional view of the anastomosis ring shown in FIG. 2A.

Referring now to FIG. 2A, there is seen a perspective view of an anastomosis ring generally referenced 30 formed such that the circular cross sectional area remains constant about the periphery of the ring. A cross-sectional view is seen in FIG. 2B as taken along line 3—3 in FIG. 2A. This constant cross-section ensures that a uniform radial force is exerted as ring 30 contracts or expands.

Figure 3A:
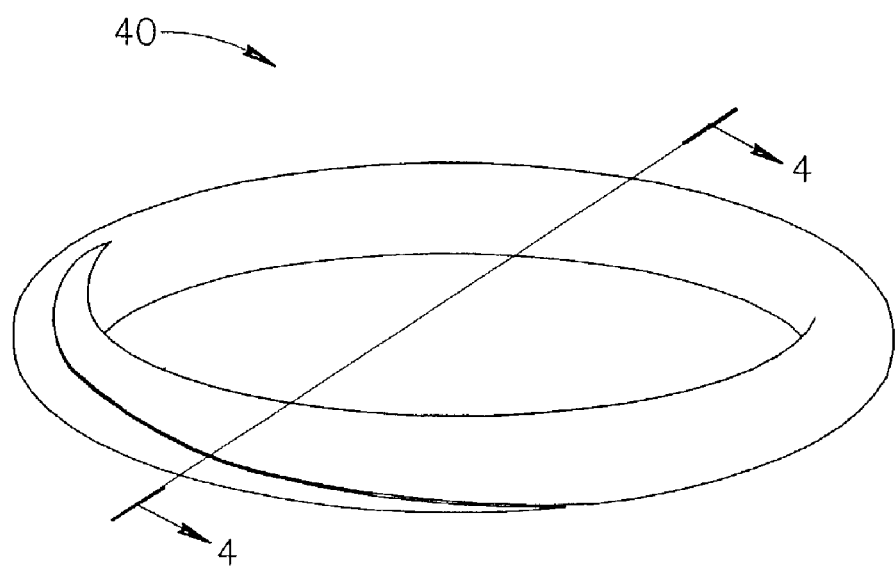
FIG. 3A illustrates a perspective view of an anastomosis ring having a constant elliptical cross-sectional area.
Figure 3B:
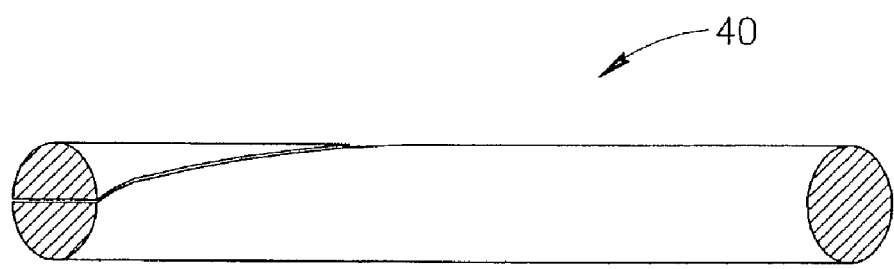
FIG. 3B illustrates a cross-sectional view of the anastomosis ring shown in FIG. 3A.

Referring now to FIGS. 3A and 3B, there is seen, respectively, a perspective and a cross-sectional view taken along line 4—4 of an anastomosis ring generally referenced 40, formed such that the elliptical cross-sectional area remains constant about the periphery of the ring, in accordance with an alternative embodiment of the present invention. This ensures that a uniform radial force is exerted as ring 40 contracts or expands. Furthermore, using, for example, various elliptical cross-sections provides a means for controlling the radial pressure exerted by ring 40.

Figure 4A:
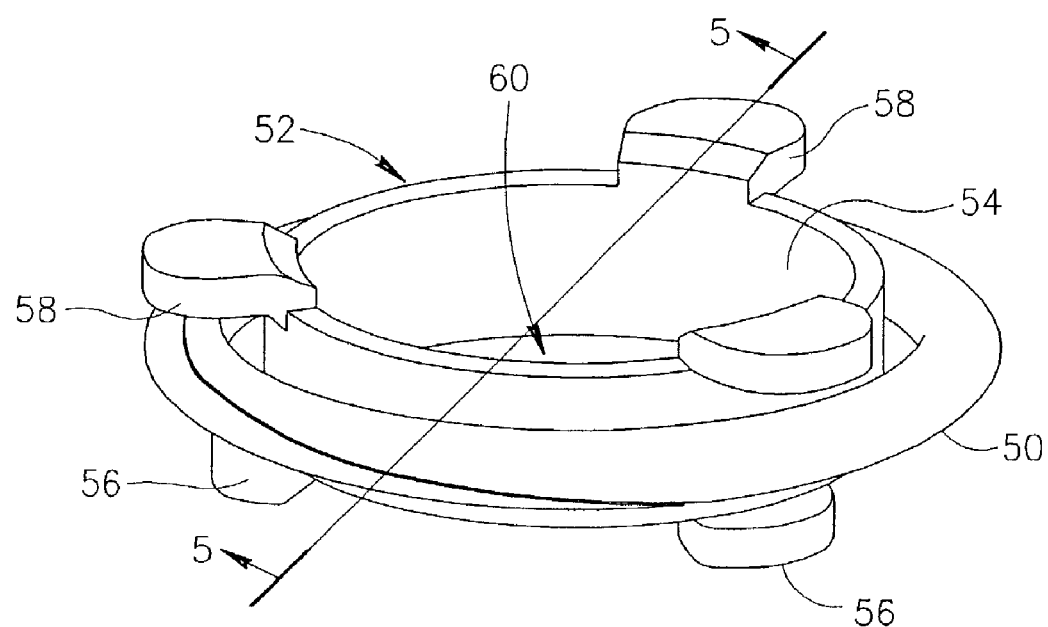
FIG. 4A illustrates a perspective view of an anastomosis ring in crimping engagement with a crimping support element in accordance with a preferred embodiment of the present invention.
Figure 4B:
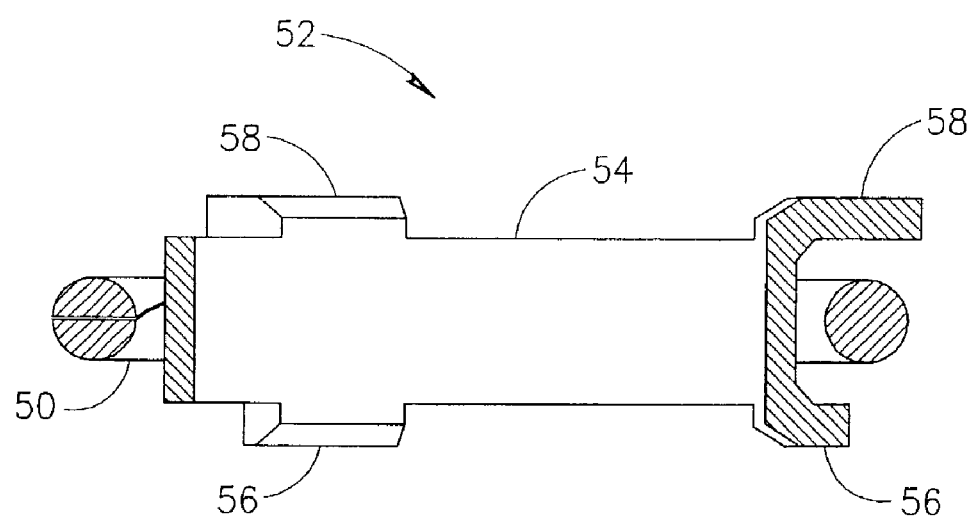
FIG. 4B illustrates a cross-sectional view of the anastomosis ring and crimping support element shown in FIG. 4A.

Referring now to FIGS. 4A and 4B, there is seen, respectively, a perspective and a cross-sectional view of a contractible anastomosis ring referenced 50 in crimping engagement with a crimping support element referenced generally 52, in accordance with a preferred embodiment of the present invention. The cross-sectional view seen in FIG. 4B is taken along line 5—5 in FIG. 4A. Crimping support element 52 includes a short cylindrical section referenced 54, proximal lugs referenced 56 and distal lugs referenced 58 (as disclosed in relarion to FIG. 9 hereinbelow). Anastomosis ring 50 is caused to contract in position in crimping engagement with organ portions (not shown) against crimping support element 52, as indicated, such that proximal and distal lugs 56 and 58, respectively, ensure that ring 50 remains in position over cylindrical section 54. Crimping support element 52 has an opening referenced 60 to permit passage therethrough.

Figure 5:
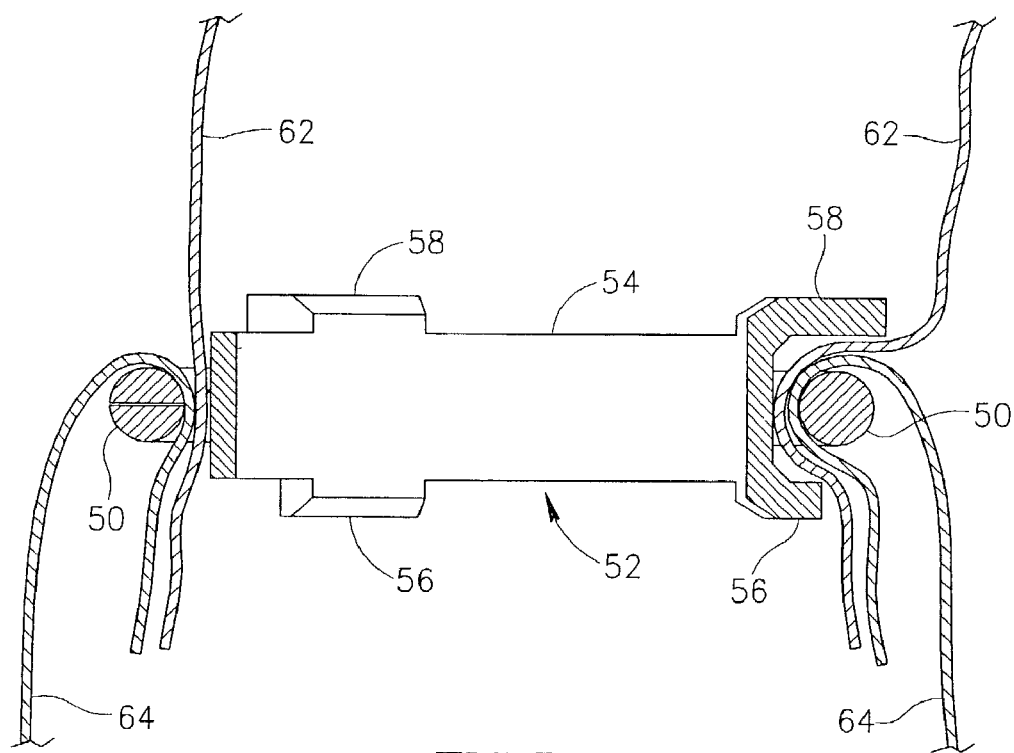
FIG. 5 illustrates a cross-sectional view of the anastomosis ring in crimping engagement with an intussuscepted organ portion and a crimping support element as shown in FIGS. 4A and 4B.

Referring now to FIG. 5, there is seen a cross-sectional view of anastomosis ring 50 in crimping engagement with organ portions referenced 62 and 64 and crimping support element 52 so as to cause anastomosis between the adjacent wall portions 62 and 64, in accordance with a preferred embodiment of the present invention. Crimping of organ portion 62 to portion 64 (as related hereinbelow with reference to FIGS. 16–23) results in anastomosis thereof. Opening 60 (as seen in FIG. 4A) in crimping support element 52 provides immediate patency to anastomosed organ portions 62 and 64.

Figure 6:
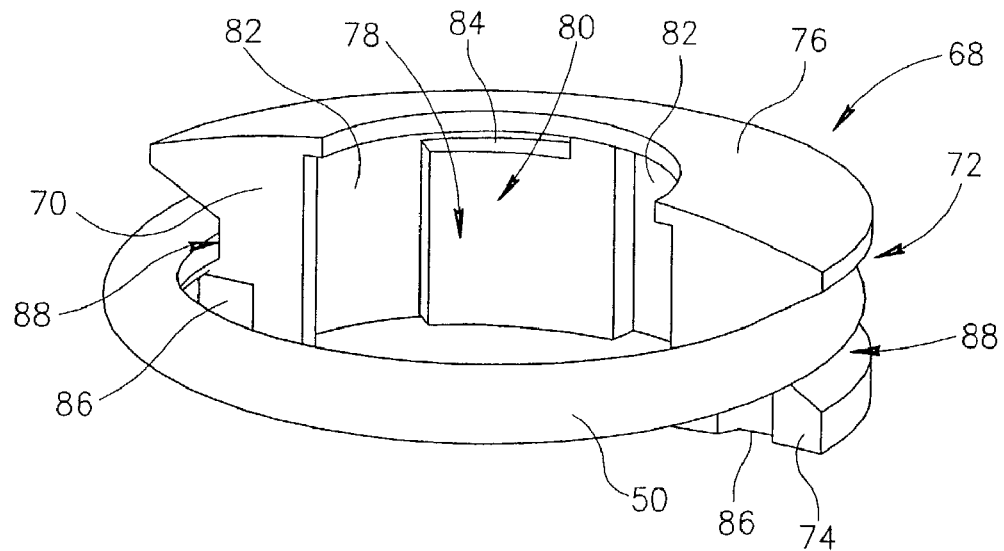
FIG. 6 illustrates a cutaway view of an anastomosis ring in crimping engagement with a crimping support element in accordance with an alternative embodiment of the present invention.

Referring also to FIG. 6, in accordance with an alternative embodiment of the present invention, there is seen a cutaway view of contractible anastomosis ring 50 (as disclosed hereinabove in relation to FIGS. 1A–3B) in crimping engagement with organ portions (not shown) against a crimping support element generally referenced 68. Anastomosis ring 50 is employed to crimp adjacent intussuscepted organ wall portions (not shown, and as related hereinbelow with reference to FIGS. 16–23) against crimping support element 68 to cause anastomosis of the organ portions. Referring further to FIG. 6, crimping support element 68, has a side-wall referenced 70 defining a generally cylindrical, outward facing surface referenced 72. Crimping support element 68, further has a proximal and a distal end wall referenced 74 and 76 respectively, (as disclosed in relation to FIGS. 11–12 hereinbelow) arranged generally transversely to side-wall 70. A generally axial aperture referenced 78 is formed through crimping support element 68 for providing flow communication therethrough after anastomosis is accomplished by crimping of adjacent organ walls with anastomosis ring 50 thereto (as disclosed hereinbelow in relation to FIGS. 16–23). Axial aperture 78 also defines an inner wall surface referenced 80 of crimping support element 68. Formed in inner wall surface 80 are bayonet engagement recesses referenced 82 and bayonet locking recesses 84 (referred to hereinbelow in relation to FIGS. 11–12). Further, retaining recesses referenced 86 are formed in proximal end wall 74. Formed in outward facing surface 72 is a circumferential recess referenced 88 to ensure precise positioning and retention of contractible anastomosis ring 50 therein.

Figure 7:
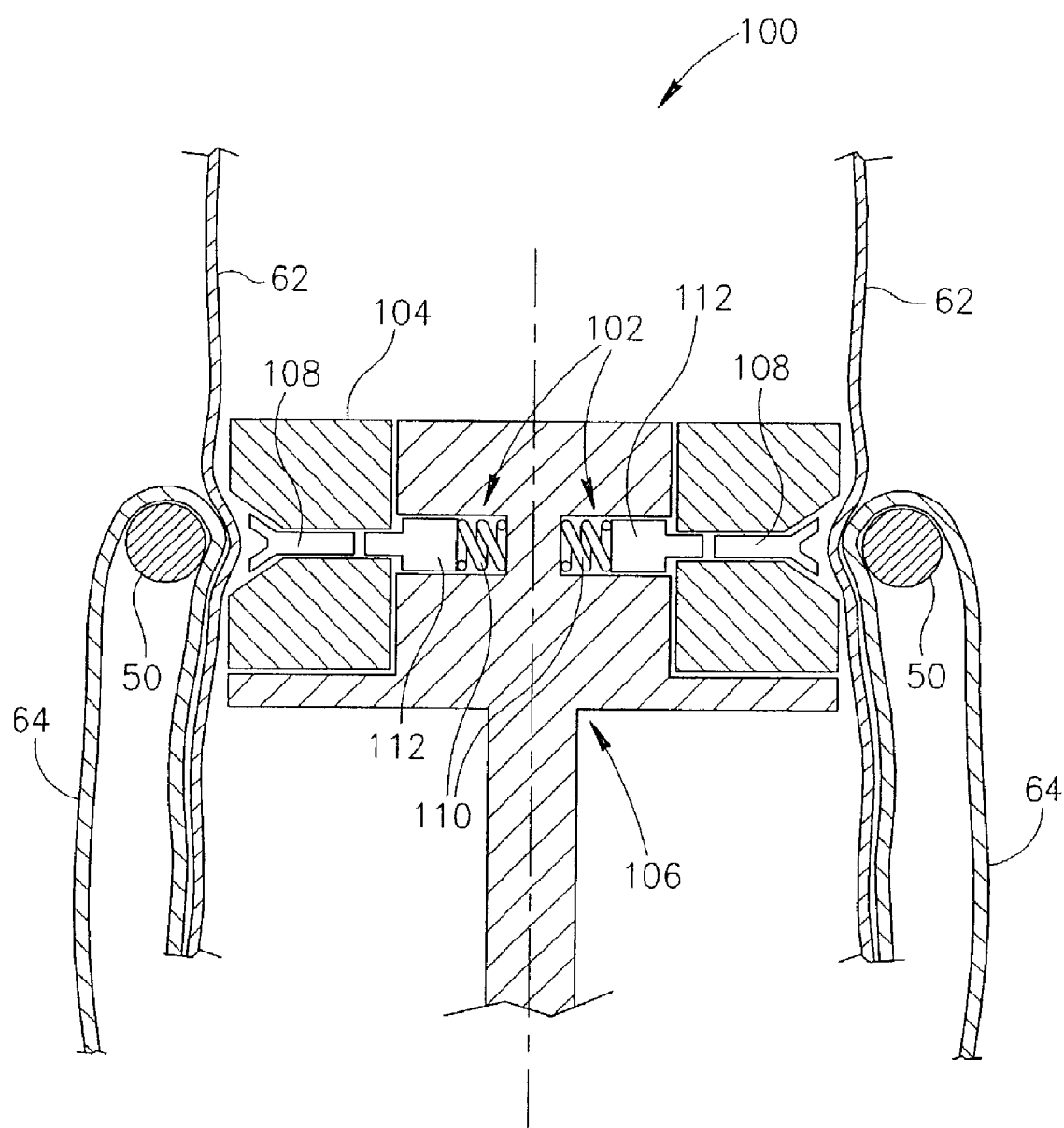
FIG. 7 illustrates a cross-sectional view of a crimping support element release mechanism in accordance with an alternative embodiment of the present invention.

Referring now to FIG. 7, in accordance with an alternative embodiment of the present invention, there is seen a crimping support element generally referenced 100 having a release mechanism generally referenced 102 formed to retain crimping support element referenced 100 to applicator member generally referenced 106 (referred to hereinbelow in relation to FIGS. 11–12). Crimping support element 104 is retained in position by retention pins 112, which are kept in a retention mode by springs referenced 110. Further, to release crimping support element 104 from applicator member 106, anastomosis ring 50 is brought into crimping engagement with organ portions 62 and 64 and crimping support element 100. Thereupon, anastomosis ring 50 depresses release pins referenced 108, which, in turn, depress retention pins 112, and thereby release crimping support element 104 from applicator member 106.

Figure 8A:
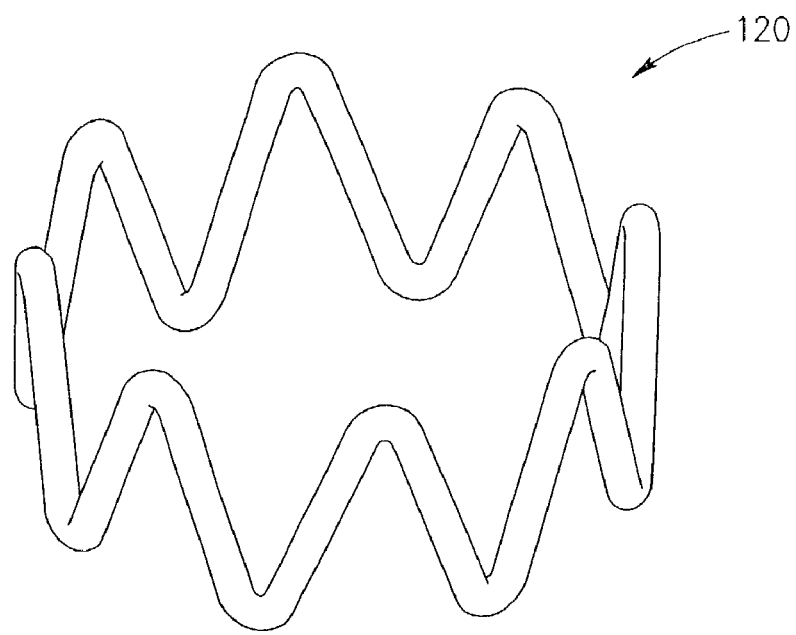
FIG. 8A illustrates a perspective view of an alternative anastomosis ring.
Figure 8B:
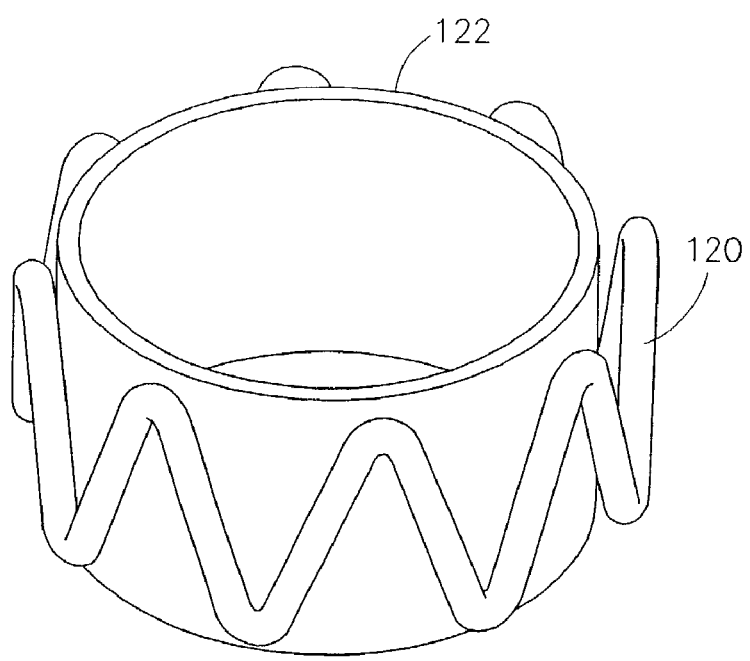
FIG. 8B illustrates the anastomosis ring as shown in FIG. 8A in crimping engagement with a cylindrical crimping support element.

Referring now to FIGS. 8A and 8B, there is seen a perspective view of an alternative anastomosis ring generally referenced 120 having a three-dimensional closed waveform. In FIG. 8B, anastomosis ring 120 is seen in crimping engagement with organ portions (not shown) against a generally cylindrical crimping support element referenced 122. Utilizing an anastomosis ring having, for example, a three-dimensional closed waveform, provides a means for controlling and specifically spreading the pressure applied to anastomosed organ portions between the ring and crimping support element and for providing a crimping force over a larger surface area, especially when a single coil ring could cause damage to organ portion walls by applying excessive pressure thereto.

Figure 9:
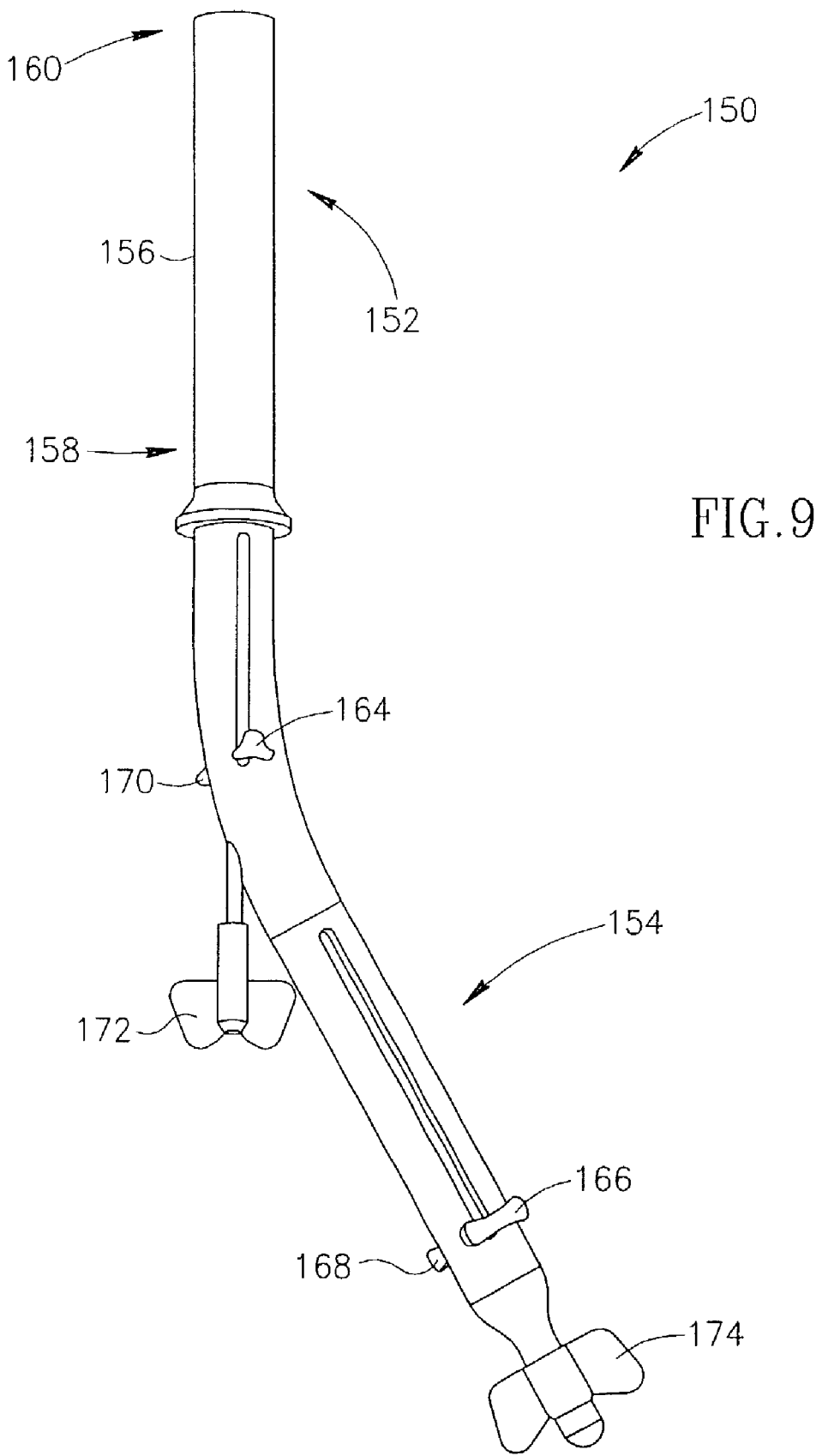
FIG. 9 illustrates an apparatus for intussusception and anastomosis in accordance with an embodiment of the present invention.

Referring now to FIG. 9, there is seen an external view of an apparatus generally referenced 150 for intussusception and anastomosis in accordance with an embodiment of the present invention. Apparatus 150 is comprised of an operative portion referenced generally 152 and a control or activating portion referenced generally 154. Operative portion 152 has an outer cylindrical enclosure referenced 156 having a proximal end generally referenced 158 and a distal end generally referenced 160. Disposed within outer cylindrical member 156 are intussusception and anastomosis apparatus (as referred to hereinbelow in relation to FIGS. 11–15). Control or activating portion 154 includes various control elements to facilitate operation of the intussusception and anastomosis apparatus. The control elements include an anastomosis ring applicator lever referenced 164, proximal and distal clamp jaw levers 166 and 168, respectively, an excising applicator lever referenced 170, crimping support applicator control referenced 172 and intussusception and anastomosis apparatus positioning controller 174. In order to carry out intussusception and anastomosis, a user (not shown) grasps control portion 154 of apparatus 150 and inserts distal end 160 of operative portion 152 a preselected distance into a hollow organ such as the bowel via the anus. It is sometimes necessary to provide controlled positioning and retraction of intussusception and anastomosis apparatus 150, (as disclosed hereinbelow in relation to FIG. 37) Included with apparatus 150, according to an alternative embodiment of the present invention, is an optical device (not shown) for providing a view of the interior of the organ being intussuscepted and anastomosed.

Figure 10:
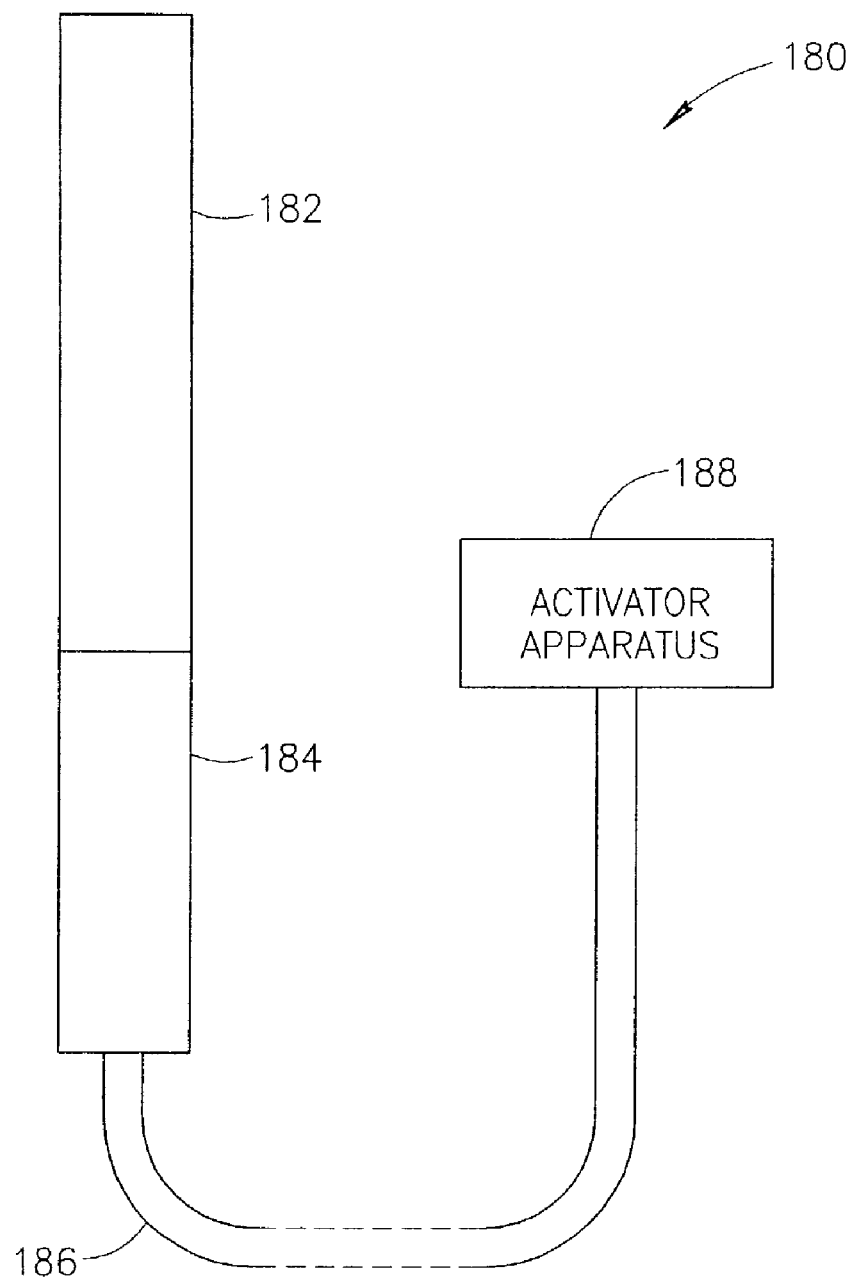
FIG. 10 illustrates a schematic view of an apparatus for intussusception and anastomosis flexibly connected to a remote operating mechanism.

Referring now to FIG. 10, there is seen, in accordance with an embodiment of the present invention, an intratubular intussusception and anastomosis apparatus generally referenced 180, including operative portion referenced 182 and operationally connected thereto operating mechanism referenced 184. A flexible control cable referenced 186 connects operating mechanism 184 to a remote activator apparatus referenced 188. Included in control cable 186, according to an alternative embodiment of the present invention, is an optical device (not shown) for providing a view of the interior of the organ being intussuscepted and anastomosed.

Figure 11:
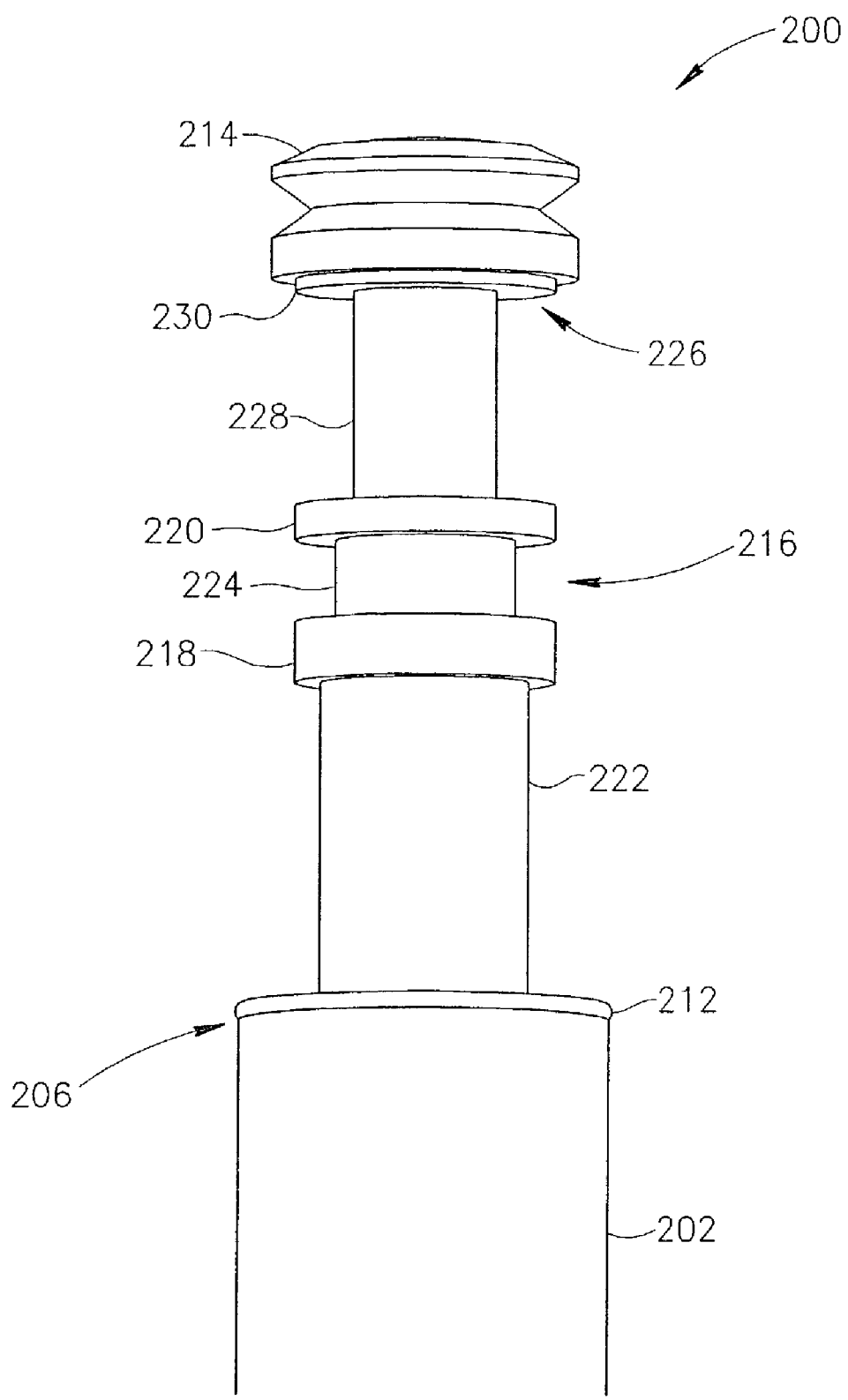
FIG. 11 illustrates a partial view of an apparatus prior to intussusception and anastomosis.
Figure 12:
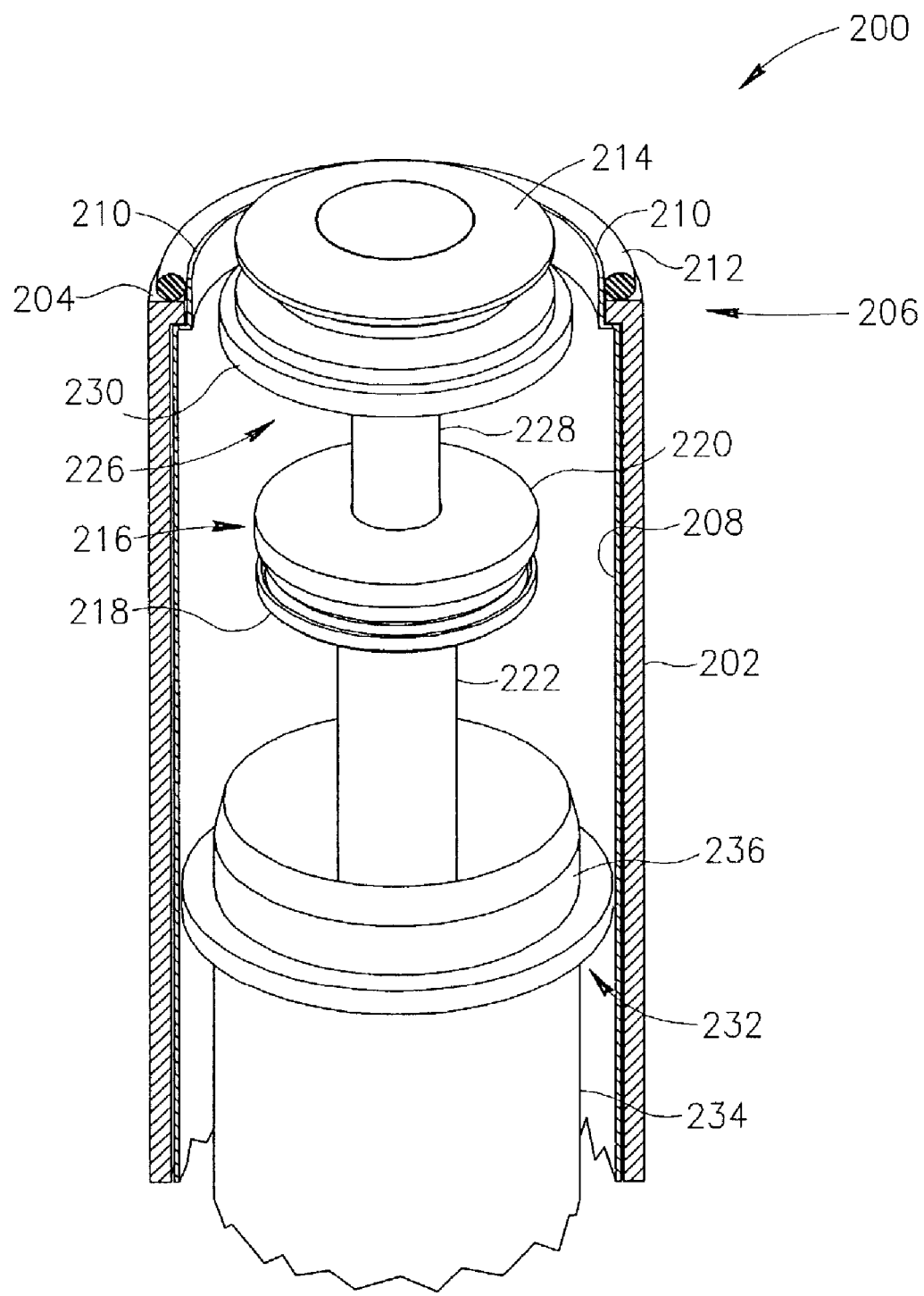
FIG. 12 illustrates a cut away view of an apparatus for intussusception and anastomosis.

With reference to FIGS. 11 and 12, in accordance with a preferred embodiment of the present invention, there is seen apparatus generally referenced 200 (generally as disclosed hereinabove as operative portion 152 in FIG. 9 and as operative portion 182 in FIG. 10) for intussusception and anastomosis of a hollow organ (not shown) from which a portion is to be excised. FIG. 12 is a cut-away view of apparatus 200 as seen in FIG. 11. Apparatus 200 has an outer, cylindrical enclosure referenced 202 having a retaining lip referenced 204 (FIG. 12) formed at the distal end generally referenced 206 thereof.

Slidably disposed within and coaxial with enclosure 202 is a generally tubular anastomosis ring applicator referenced 208 (FIG. 12), having a recessed portion referenced 210 at the distal extremity thereof, thereby to demountably engage an anastomosis ring referenced 212 thereto (as referred to hereinabove in relation to FIGS. 1A–3B and 8A). Ring applicator 208 is either rigidly or flexibly operatively connected to a control device (not shown, as disclosed hereinabove with reference to FIGS. 9–10) to cause an advancing and retracting movement of ring applicator 208. Ring applicator 208 is advanced to facilitate demountably engaging expanded anastomosis ring 212 thereto while precooled below the transition temperature and in a malleable or plastic state (as disclosed hereinabove in relation to FIGS. 1A–1D). Ring 212 is permitted or caused to warm so as to reach and exceed the transition temperature, thereby reverting to a contractible elastic state. Thereafter, by retracting ring applicator 208, anastomosis ring 212 is disengaged from ring applicator recess 210 thereby crimping adjacent organ walls to crimping support element referenced 214 which has been pre-aligned with lip 204 (as disclosed hereinbelow in relation to FIGS. 18–19).

Further, there is seen an intratubular intussusception device, generally referenced 216 disposed coaxially within enclosure 202, for intussusception of a preselected hollow organ portion to be excised from the hollow organ (as disclosed hereinbelow with reference to FIGS. 16–17). Intussusception device 216 includes proximal and distal clamping jaws referenced 218 and 220, respectively.

In accordance with one embodiment of the present invention, circular clamping jaws 218 and 220 are slidingly operable in accordance with movements of coaxial operating supports referenced 222 and 224, respectively, beyond and retractable within enclosure 202 and ring applicator 208. Jaws 218 and 220 are caused to move axially with respect to enclosure 202 to be disposed at a preselected mid-position relative to a diseased organ portion (as referred to hereinbelow with reference to FIG. 16). After drawing substantially the mid-portion of the diseased organ portion to within jaws 218 and 220, distal jaw 220 is retractable relative to proximal jaw 218 and, similarly, proximal jaw 218 is advancible relative to distal jaw 220, so as to clamp a preselected organ portion (as disclosed hereinbelow with reference to FIG. 16). Thereafter, intussusception of the preselected organ portion occurs by simultaneously retracting jaws 218 and 220 to within enclosure 208 (as disclosed hereinbelow with reference to FIG. 17).

Activating or control means (not shown; as disclosed hereinabove with reference to FIGS. 9–10) for intussusception is operationally connected to coaxial clamping jaws 218 and 220 which are operative independently or in clamping engagement by operating supports 222 and 224 thereby to advance or retract clamping jaws 218 and 220. This activating means is disposed at a proximate end of apparatus 200 or remotely therefrom (not shown; as disclosed hereinabove with reference to FIGS. 9–10), in accordance with embodiments of the present invention. According to alternative embodiments of the present invention, (as disclosed hereinbelow in relation to FIGS. 13–14) there are alternative intussusception clamping devices, wherein clamping movement of proximal and distal jaws 218 and 220 is caused without necessitating independent movement of supports 222 and 224, respectively.

In accordance with a preferred embodiment of the present invention, there is also seen in FIGS. 11–12 a crimping support applicator member generally referenced 226, which is slidingly disposed coaxially within coaxial clamp supports 222 and 224 and operating supports (not shown) therewithin. Crimping support applicator member 226 is configured as a tubular support shaft referenced 228 having a transverse holder referenced 230 formed at the distal end thereof. Crimping support element 214 (as disclosed hereinabove with reference to FIGS. 4A–8B) is demountably fastened to transverse holder 230. Crimping support applicator member 226 has activating means (not shown; as disclosed hereinabove with reference to FIGS. 9–10) according to embodiments of the present invention, which are operationally connected directly or remotely to crimping support applicator member 226 to facilitate advancment or retraction thereof.

According to an alternative embodiment of the present invention, crimping support element 214 (as disclosed hereinabove in relation to FIG. 6), is demountably fastened to an alternatively configured crimping support applicator member, by means of a bayonet fastening mechanism (not shown) formed at a distal end thereof. Bayonet fastening mechanism of crimping support applicator member 226 is engaged into bayonet engagement recesses 82 and locked into bayonet locking recesses 84 of crimping support element 68 (seen in FIG. 6), by rotating an inner coaxial shaft (not shown) within tubular support shaft 228: Activating means (not shown, as disclosed hereinabove with reference to FIGS. 9–10) for operating crimping support applicator member 226, according to embodiments of the present invention, are operationally connected directly or remotely to crimping support applicator member 226.

In accordance with a preferred embodiment of the present invention, an intratubular anastomosis crimping support element 214 is aligned with lip 204. Thereafter, anastomosis ring 212 (as referred to hereinabove in relation to FIGS. 1A–3B) disengages from anastomosis ring applicator recess 210, and thereby crimps adjacent intussuscepted wall portions of a hollow organ (not shown) against crimping support element 214 (as disclosed hereinbelow with reference to FIGS. 18–19).

In FIGS. 11–12, in accordance with a preferred embodiment of the present invention, there is further seen a surgical excising means generally referenced 232 (FIG. 12), including an excise applicator referenced 234. Distally attached thereto is a cylindrical cutting blade referenced 236, operatively associated with transverse holder 230 of crimping support applicator member 226. Following intratubular intussusception and crimping of adjacent organ wall portions with anastomosis ring 212 against crimping support element 214, cylindrical cutting blade 236 is selectably operable to excise the diseased organ portion (as disclosed hereinbelow in relation to FIG. 20). Excise applicator 234 is distally advanced towards transverse holder 230 until reaching operative engagement therewith. Activating means (not shown; as disclosed hereinabove in relation to FIGS. 9–10) for surgical excising means 232 is operationally connected thereto, either directly or remotely. In accordance with an alternative embodiment of the present invention, another example of a surgical excising means is disclosed hereinbelow in relation to FIG. 15.

Figure 13:
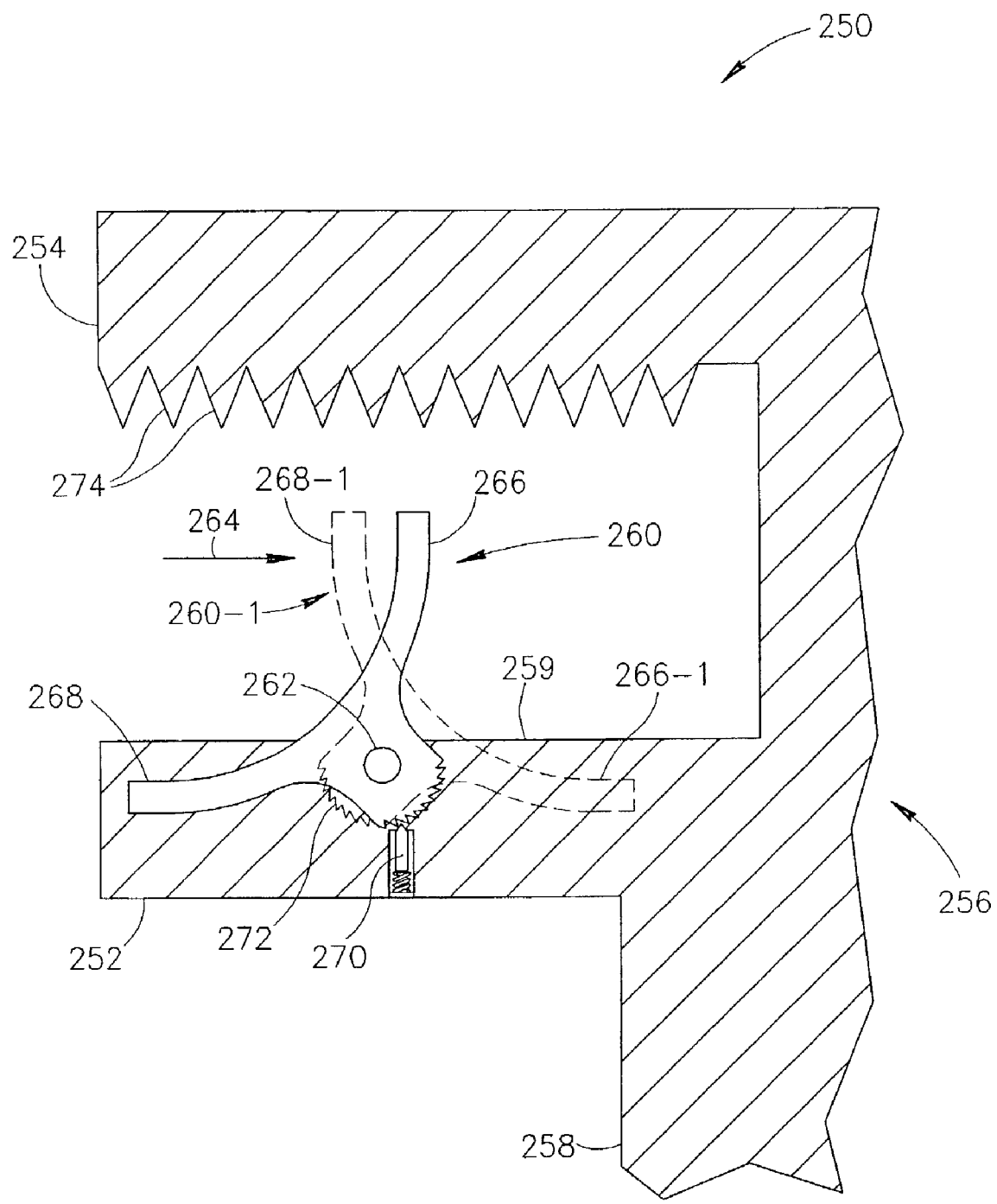
FIGS. 13–14 illustrate clamping mechanisms in accordance with alternate embodiments of the present invention.
Figure 14:
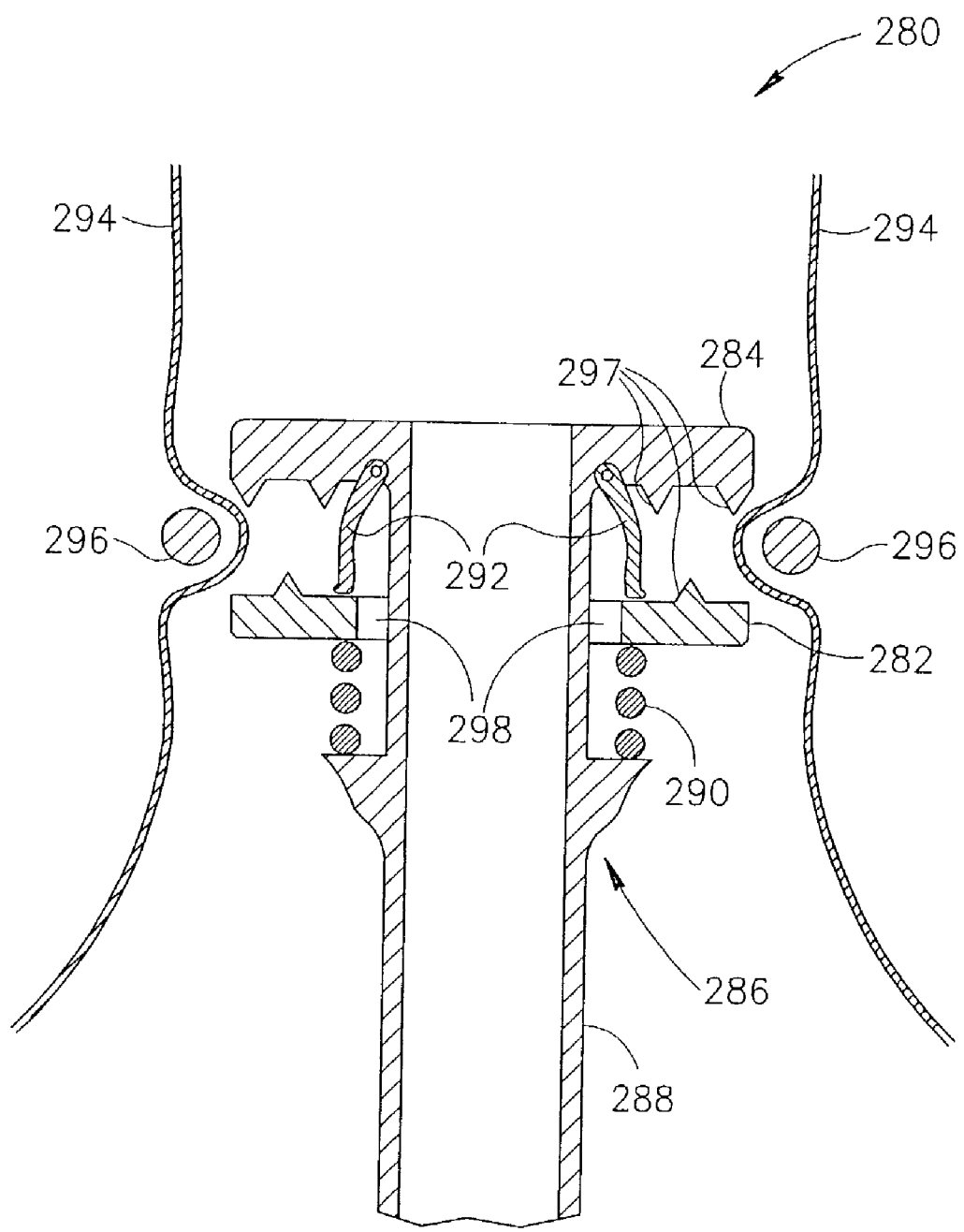

Referring now to FIGS. 13–14 there are seen additional configurations of clamping jaw mechanisms in accordance with alternate embodiments of the present invention. The clamping between proximal and distal jaws 218 and 220, respectively, is caused without necessitating independent movement of supports 222 and 224 respectively (as disclosed hereinabove in relation to FIGS. 11–12). There is seen in FIG. 13 a toggle clamping apparatus generally referenced 250, including circular proximal and distal jaws 252 and 254 respectively, fixably connected to a distal end generally referenced 256 of a common clamping support shaft referenced 258. Proximal jaw 252 includes, disposed in surface referenced 259, a preselected number of toggle clamps referenced 260, each rotationally mounted on a pivot pin referenced 262. Toggle clamp 260 rotates to position 260-1 as a result of a force applied in the direction of arrow 264 to arm 266, which thereupon rotates to position 266-1. In sympathy therewith, arm referenced 268 rotates to position referenced 268-1 and is held in this position by a spring-operated ratchet pin referenced 270 which operatively engages ratchet teeth referenced 272. Distal jaw 254 includes concentric rings referenced 274 formed facing towards proximal jaw 252. When an organ portion (not shown) to be subjected to intussusception and anastomosis is drawn between jaws 252 and 254 in the direction of arrow 264, consequent to the resulting force exerted on arm 266, toggle clamp 260 rotates to position 260-1 such that arm 268 moves to position 268-1. The drawn-in organ portion is thereby clamped against distal jaw 254 and held in position by rings 274 in preparation for intussusception of the organ portion.

In accordance with another embodiment of the present invention, there is seen, in FIG. 14, a spring-loaded clamping apparatus generally referenced 280. A proximal and a distal circular jaw referenced 282 and 284, respectively, are disposed at a distal end referenced generally 286 of a common clamping support shaft referenced 288, distal jaw 284 being fixably attached thereto. Proximal jaw 282 is slidingly and elastically mounted on clamping support shaft 288, supported by springs referenced 290, thereby causing proximal jaw 282 to elastically engage distal jaw 284 in a clamping configuration. To maintain a predetermined separation between jaws 282 and 284, there are disposed therebetween two or more stay members referenced 292, rotationally attached to distal jaw 284 and engaging proximal jaw 282. The clamping of organ portion referenced 294 is effected by suture referenced 296 drawing organ portion 294 inward between jaws 282 and 284. Stay members 292 are radially depressed in an axial direction, such that they pass through apertures referenced 298, permitting proximal jaw 282 to move elastically toward distal jaw 284 and to hold organ portion 294 in a clamping engagement therebetween. There are also formed, in jaws 282 and 284, a series of concentric rings referenced 297, disposed therebetween to retain a grip on organ portion 294 prior to intussusception thereof.

Figure 15:
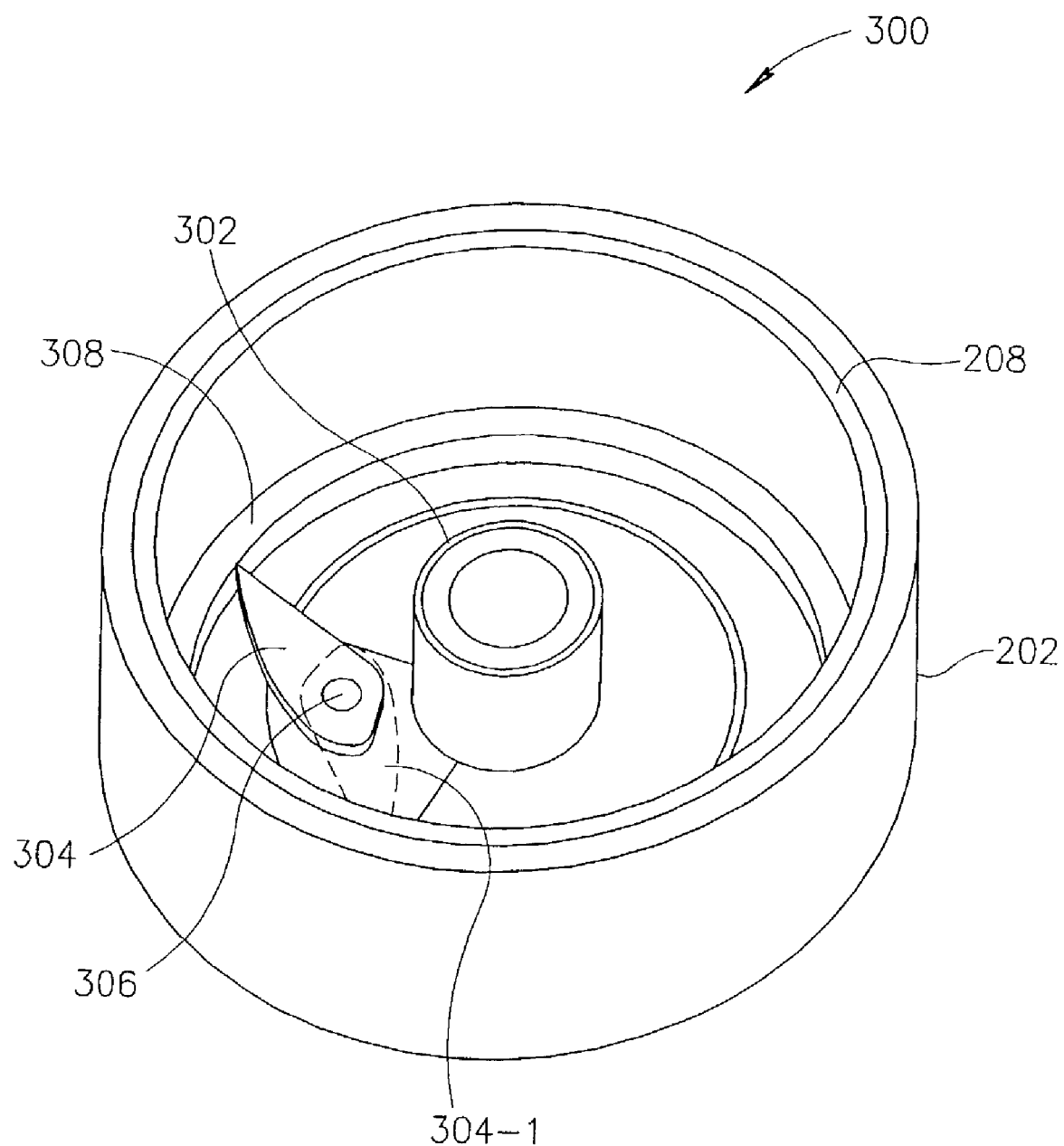
FIG. 15 illustrates a rotating cutting blade according to an alternative embodiment of the present invention.

In accordance with an alternative embodiment to the present invention, referring now to FIG. 15, there is seen an alternative surgical excising means referenced generally 300. This includes an axially rotary excise applicator referenced 302 coaxially disposed within outer cylindrical enclosure 202 (as disclosed hereinabove in relation to FIGS. 11–12), having distally attached thereto a cutting blade referenced 304, pivotally attached to pivot pin referenced 306. Cutting blade 304 is operatively associated with a cutting anvil element referenced 308 axially slidably disposed within anastomosis ring applicator 208 (as disclosed hereinabove in relation to FIGS. 11–12). Following intratubular intussusception and crimping of the adjacent organ wall portions with an anastomosis ring against a crimping support element (not shown; as disclosed hereinbelow in relation to FIGS. 16–19), cutting blade 304 is selectably operable to excise the diseased organ portion (as disclosed hereinbelow in relation to FIG. 20). By rotation of rotary excise applicator 302, blade 304 pivots as shown, from a non-operative position referenced 304-1 and engages intussuscepted organ portions (not shown) in a cutting engagement against anvil 308. Activating means (not shown) for surgical excising means 300 is operationally connected thereto, either directly or remotely (as disclosed hereinabove with reference to FIGS. 9–10).

Figure 16:
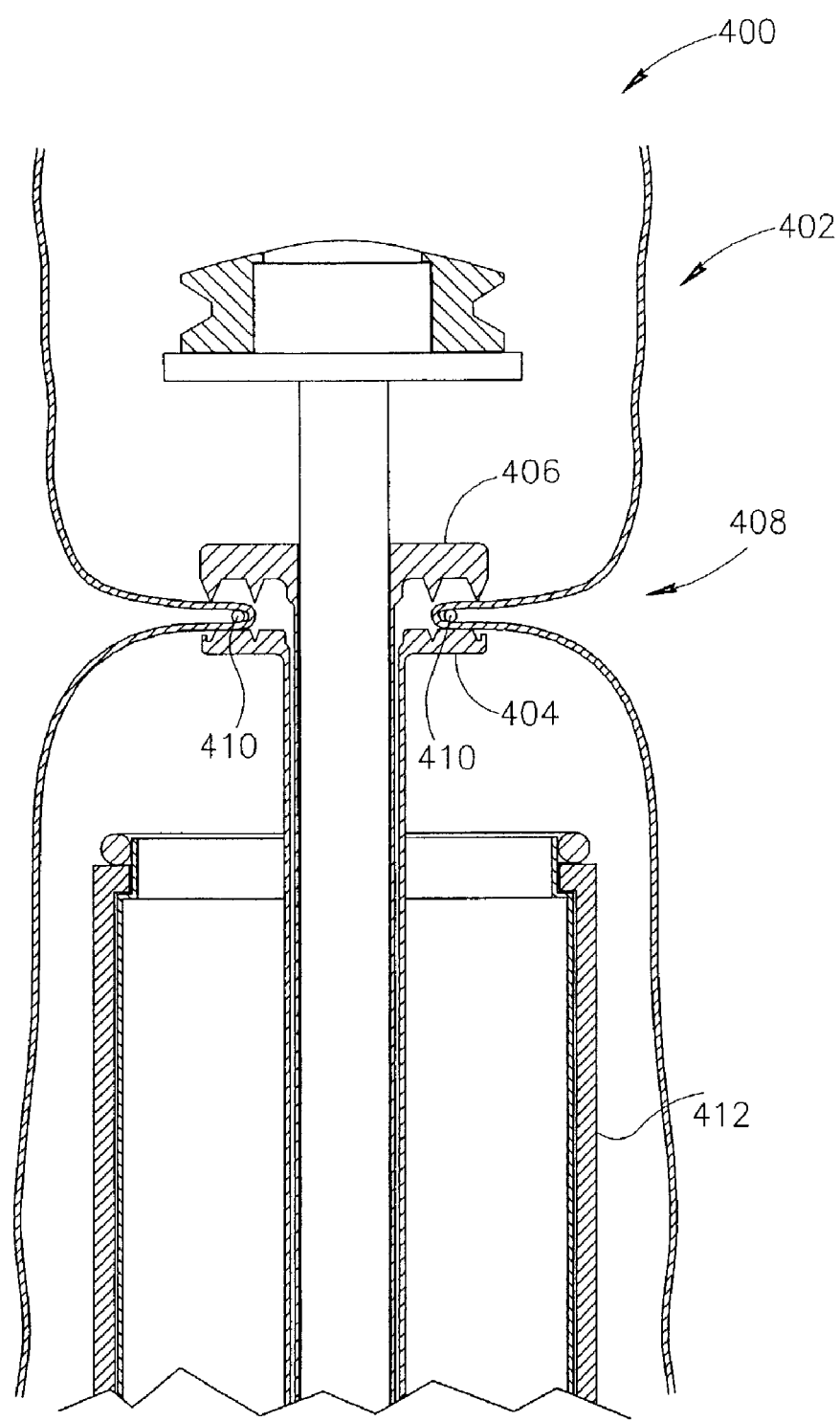
FIG. 16 illustrates a partial cross-sectional view of bowel drawn into the clamping means of the present invention.
Figure 17:
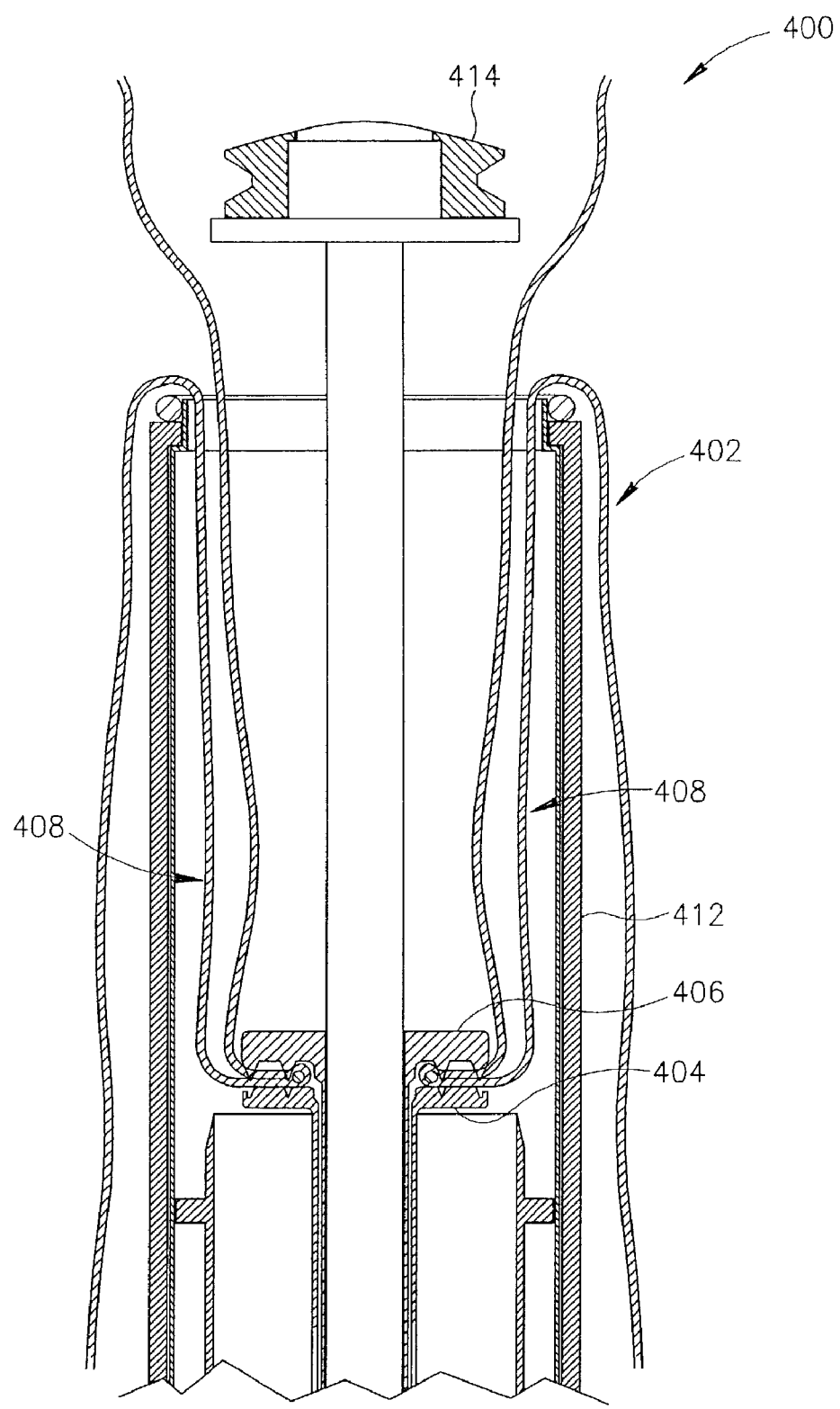
FIG. 17 illustrates a cross-sectional view of an intussuscepted bowel.

Referring now to FIGS. 16–23, in accordance with embodiments of the present invention, the method for performing an intussusception and anastomosis procedure to excise a diseased portion of a hollow organ follows hereinbelow. In FIG. 16 there is seen a cross-sectional view of apparatus generally referenced 400 for intussusception and anastomosis (generally as disclosed hereinabove in relation to FIGS. 11–12). Apparatus 400 is disposed within a hollow organ generally referenced 402, such that proximal clamp jaw 404 and distal clamp jaw 406 are aligned with substantially the middle of an organ portion referenced generally 408, of hollow organ portion 402, to be excised. Utilizing either Laproscopic or open surgery, substantially the middle of organ portion 408 to be excised is drawn within clamping jaws 404 and 406 by means of an external tie referenced 410. Jaws 404 and 406 are brought into clamping engagement with the drawn in organ portion 408.

Distal jaw 406 is retracted or proximal jaw 404 is advanced to cause the middle of organ portion 408 to be clamped between jaws 404 and 406 as shown. Thereupon, jaws 404 and 406 are simultaneously retracted while remaining in a clamping configuration to within enclosure 412 as seen in FIG. 17, causing intussusception of organ portion 408 of organ 402. Additionally, there is seen, in FIG. 18, crimping support element 414 retracted so as to align circumferential recess 416 therein with the distal lip 418 of enclosure 412.

Figure 19:
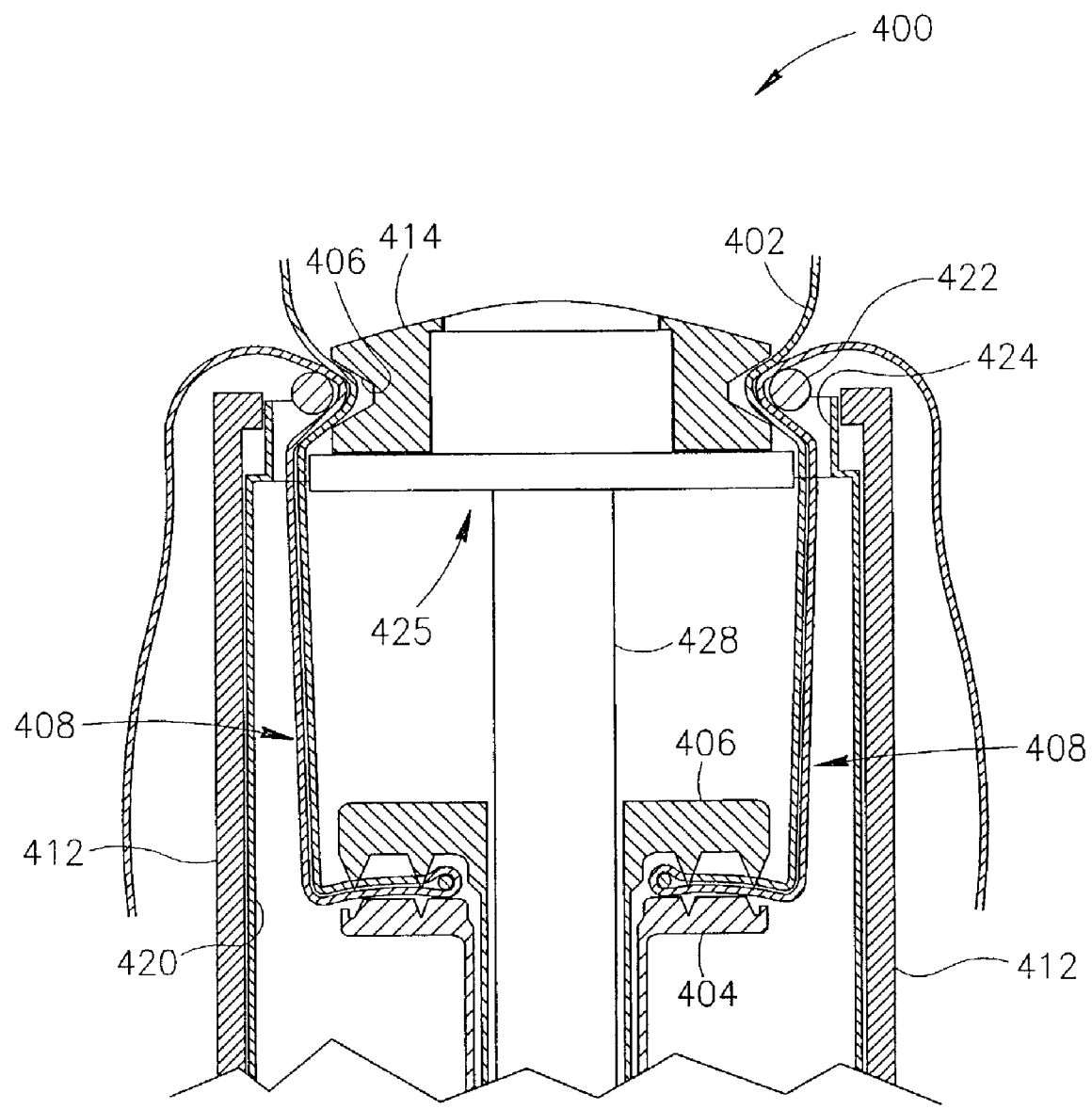
FIG. 19 illustrates a cross-sectional view of an intussuscepted bowel crimped between an anastomosis ring and a crimping support element.
Figure 20:
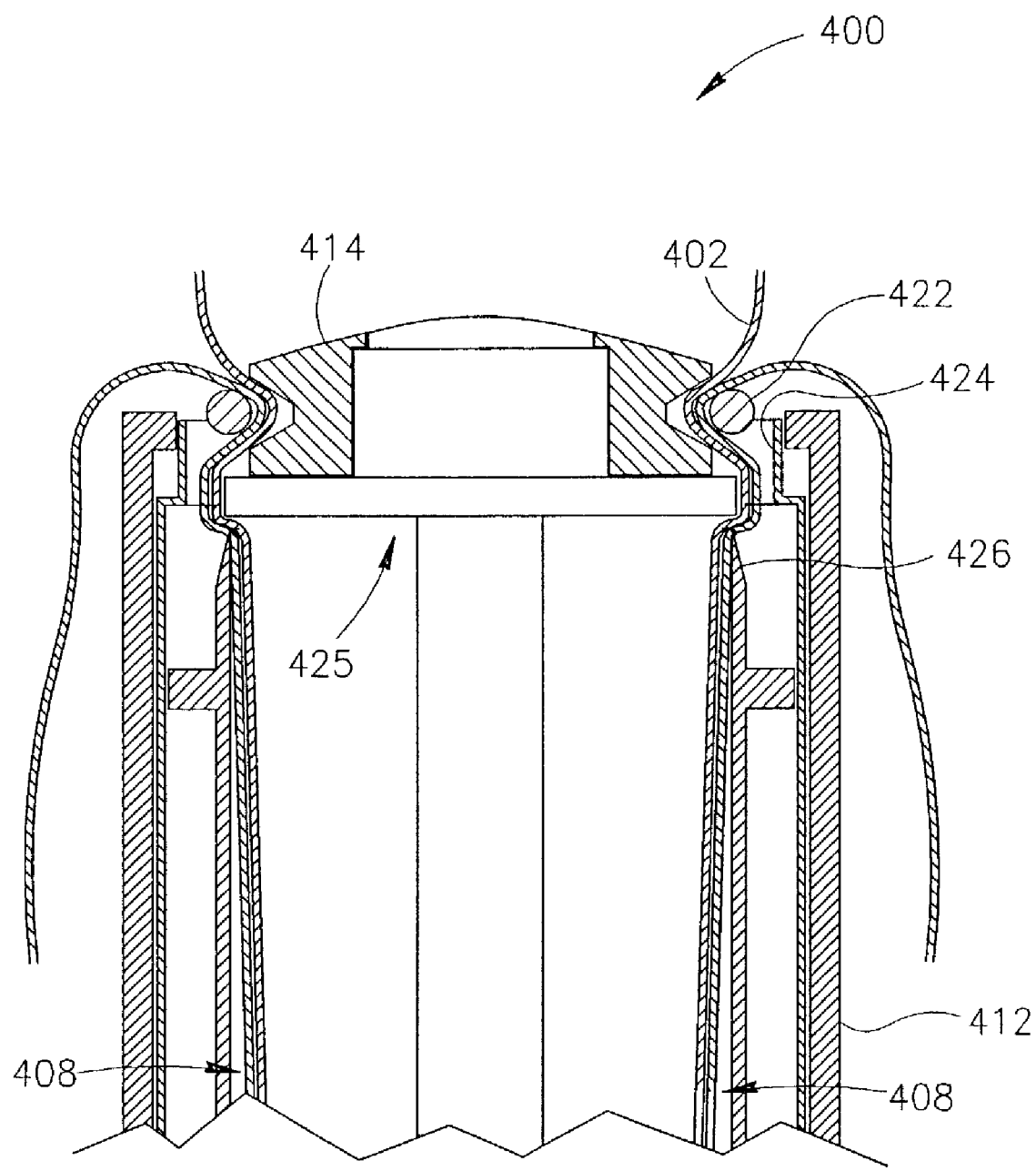
FIG. 20 illustrates a cross-sectional view of cylindrical cutting blade in cutting engagement with an intussuscepted bowel in accordance with a preferred embodiment of the present invention.
Figure 21:
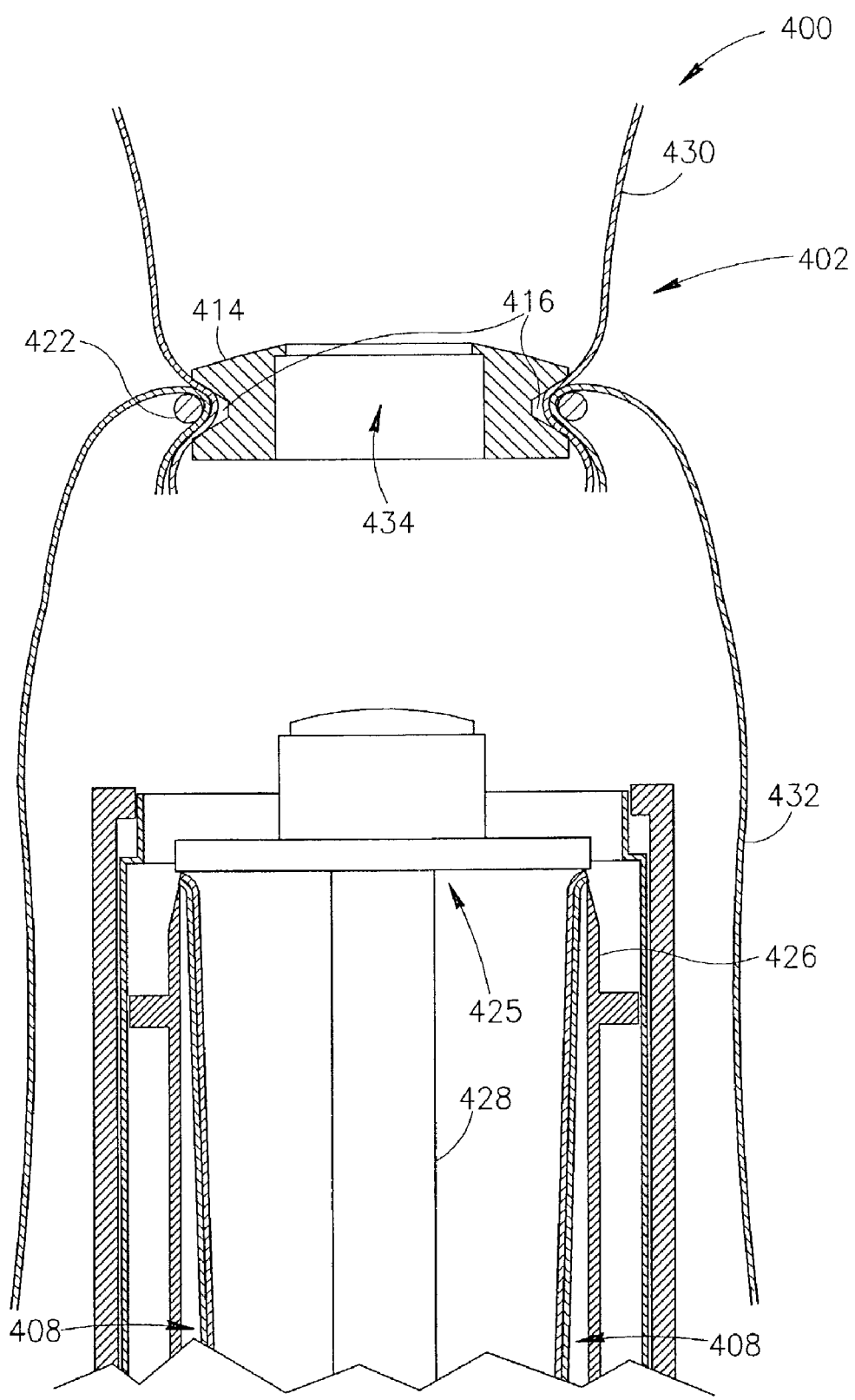
FIG. 21 illustrates a cross-sectional view of the disengaged anastomosis ring and crimping support element joining organ walls.

As seen in FIG. 19, anastomosis ring applicator 420 is slidingly retracted. Thereupon, anastomosis ring 422 is disengaged from ring applicator recess 424 and crimps adjacent organ wall portions 408 against crimping support element 414 thereby to effect anastomosis of adjacent organ wall portions 408. As seen in FIG. 20, by advancing cutting blade 426 along the axis of apparatus 400, cylindrical cutting blade 426 is brought into cutting engagement with intussuscepted organ wall portion 408, in accordance with a preferred embodiment of the present invention. Further, as seen in FIG. 21, apparatus 400 is withdrawn from organ 402, causing anastomosis ring 422 and crimping support element 414 to disengage from crimping support applicator member 425.

According to an alternative embodiment of the present invention, tubular support shaft 428 (FIG. 21) is rotated thereby to disengage the bayonet fastening mechanism (not shown) formed at a distal end of the alternatively configured crimping support applicator member 425, from bayonet locking recesses 84 and engagement recesses 82 of crimp support element 68 (as disclosed hereinabove in relation to FIG. 6). Retracting apparatus 400 causes disengagement of crimp support element 414 from crimping support applicator member 425.

Figure 22:
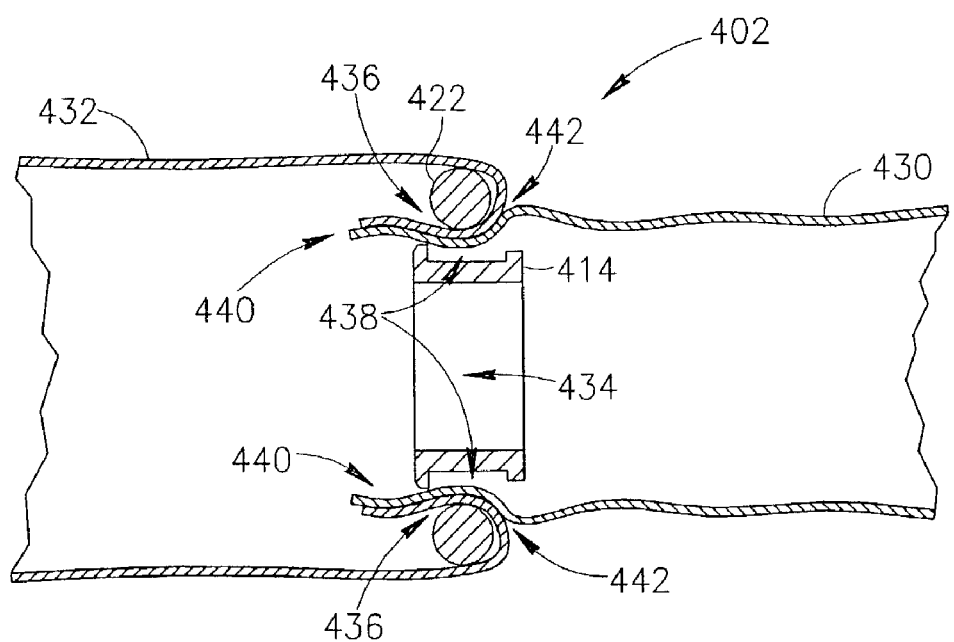
FIG. 22 illustrates a cross-sectional view of an anastomosed bowel with the anastomosis ring and crimping support element providing patency to the bowel.

As seen in FIG. 22, anastomosis ring 422, by crimping adjacent organ portions against crimping support clement 414, provides immediate patency to organ 402, bringing portions referenced 430 and 432 into flow communication through axial aperture referenced 434 of crimping support element 414. Organ 402 remains sealed to flow or leakage into the surrounding peritoneal cavity (not shown).

As a result of the pressure exerted by anastomosis ring 422 on wall portions 430 and 432 of organ 402, respective wall areas referenced 436 and 438 are pressed tightly against each other. Blood supply to end wall portions 440 and to areas 436 and 438 ceases, resulting in eventual necrosis of wall areas 436, 438 and 440. While these begin to die-off, wall tissue portions referenced 442, immediately externally adjacent thereto, begin anastomosis such that portions 442 of wall portions 430 and 432 of organ 402 become joined, and function as one continuous organ.

Figure 23:
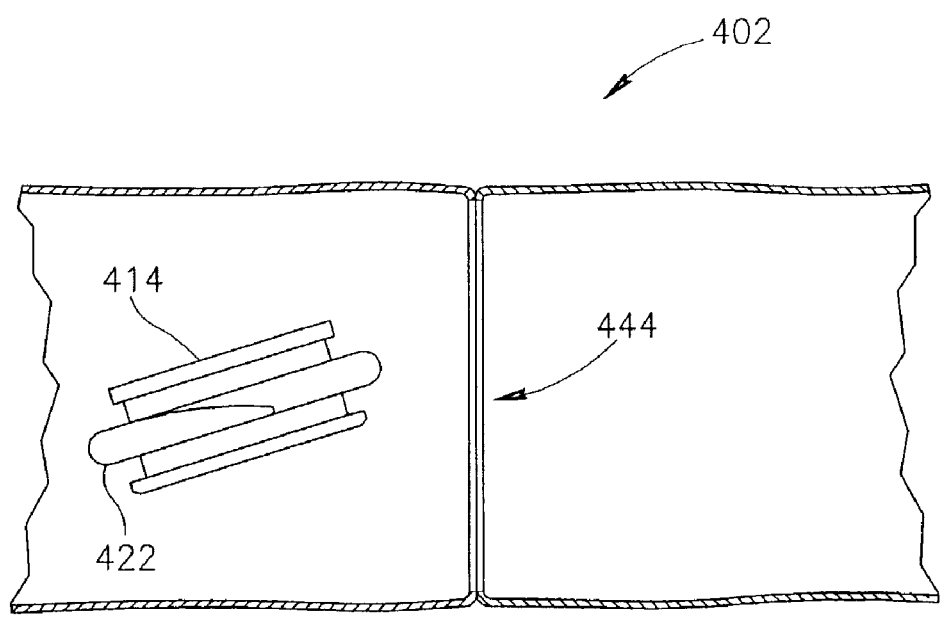
FIG. 23 illustrates a cross-sectional view of an anastomosed bowel after the anastomosis ring and crimping support element become detached therefrom.

Referring now to FIG. 23, once wall areas 436, 438 and 440 become fully necrotic, these areas together with anastomosis ring 422 and crimping support element 414 become separated from wall portions 430 and 432. This results in an aperture referenced 444 in organ 402 substantially similar to the original opening in organ 402, providing little or no restriction to normal organ flow. Necrotic wall areas 436, 438 and 440 together with anastomosis ring 422 and crimping support element 414 are passed out of organ 402, by normal organ activity.

With regard to embodiments of the present invention disclosed hereinabove, the relationship between the anastomosis ring and crimping support element relates to having a crimping support element within the anastomosed organ walls and a contractible anastomosis ring external to the organ walls. The anastomosis ring is brought into contracting crimping engagement with the organ walls against the crimping support element. In accordance, with additional embodiments of the present invention, an expandable anastomosis ring is disposed within an organ to be anastomosed and brought into crimping engagement with an external crimping support element.

Figure 24:
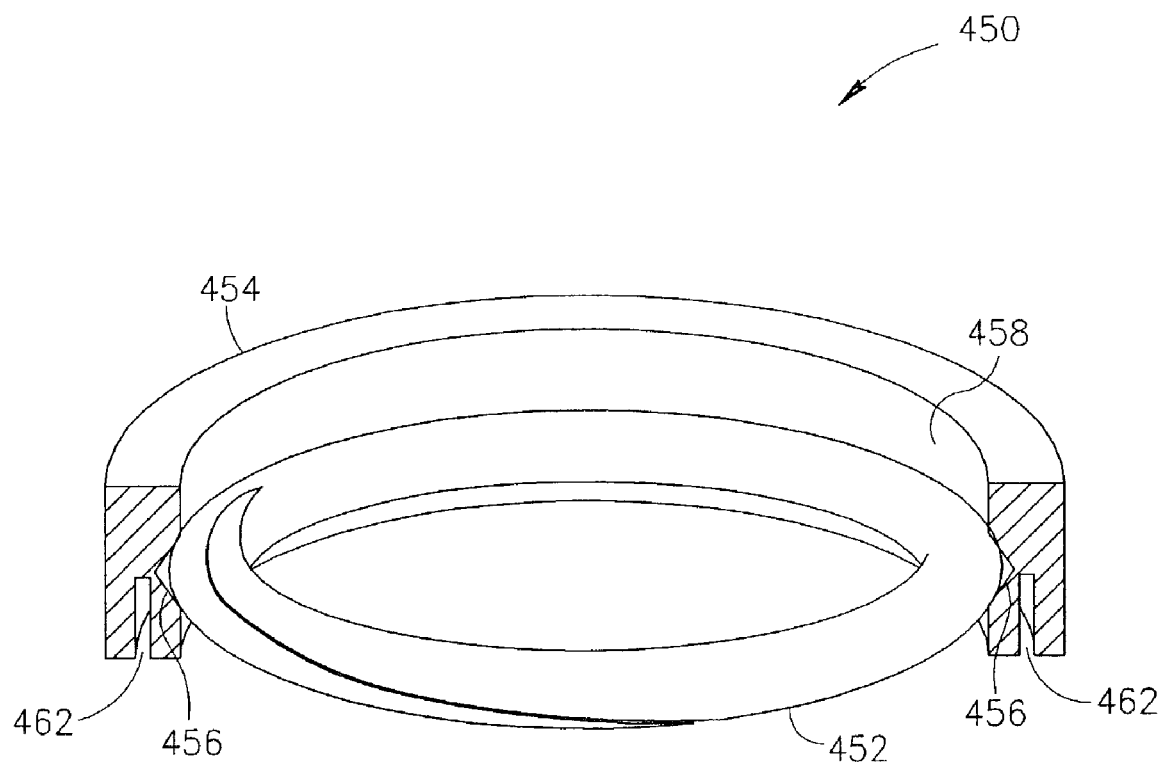
FIG. 24 illustrates a partial cross-sectional view of an expandable anastomosis ring in crimping engagement with an external crimping support element.

Referring now to FIG. 24, there is seen an alternative configuration of anastomosis ring and crimp support element, generally referenced 450 including an anastomosis ring referenced 452 in crimping engagement with an organ (not shown) against a generally cylindrical external crimping support element referenced 454. External crimping support element 454 has a retaining recess referenced 456 formed in an interior surface referenced 458 to ensure that anastomosis ring 452 remains engaged therein, and a mounting recess referenced 462 (as disclosed further herein below in relation to FIG. 25).

Figure 25:
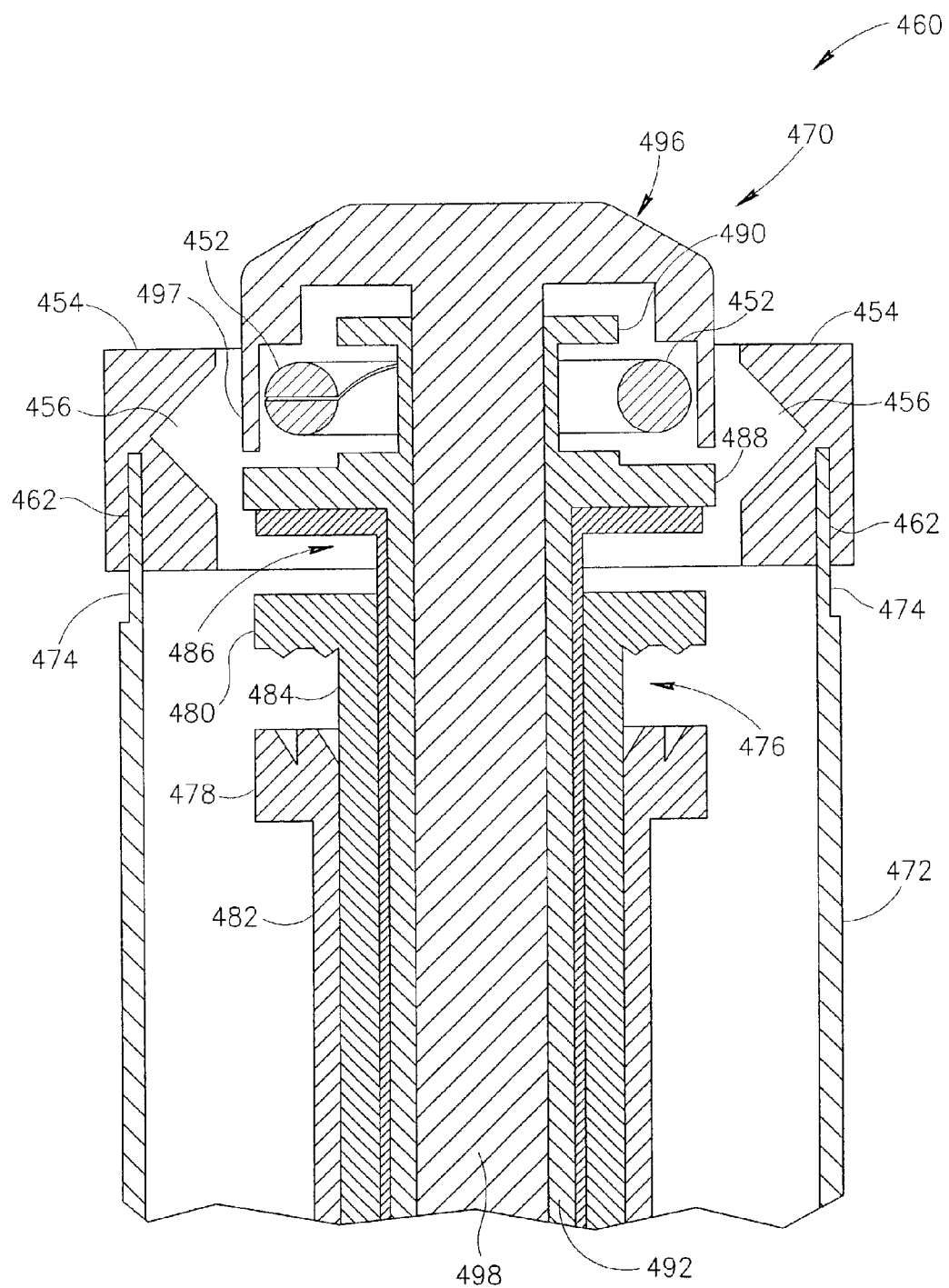
FIG. 25 illustrates an anastomosis release mechanism for applying the expandable anastomosis ring and the external crimping support element as shown in FIG. 24.

Referring now to FIG. 25, there is seen an intussusception and anastomosis apparatus, generally referenced 460, including anastomosis apparatus generally referenced 470 for causing anastomosis of portions of a hollow organ (not shown) by bringing an intratubular expandable anastomosis ring 452 into a crimping engagement with organ wall portions (not shown) against external crimping support element 454 (as disclosed hereinabove in relation to in FIG. 24). Crimping support element 454 is demountably attached to cylindrical enclosure referenced 472 by engaging mounting projections referenced 474 thereof into mounting recess 462 of crimping support element 454. Coaxially disposed within cylindrical enclosure 472 there is an intussusception apparatus generally referenced 476 which includes proximal and distal clamping jaws respectively referenced 478 and 480 operatively attached to coaxial tubular clamp operating members respectively referenced 482 and 484 to bring jaws 478 and 480 into clamping engagement with an organ portion (not shown). Further, coaxially disposed within enclosure 472 there is anastomosis apparatus 470 including an anastomosis ring mounting member referenced generally 486, which includes proximal and distal anastomosis ring holders respectively referenced 488 and 490, axially operable by a coaxial slidingly operable tubular mounting shaft referenced 492.

In order to position expandable anastomosis ring 452 between holders 488 and 490 as indicated, anastomosis ring 452 is cooled to or below the transition temperature so as to become expandably malleable. To prevent expandable anastomosis ring 452 from expanding away from mounting member 486, there is a coaxial ring applicator member generally referenced 496 having a retaining member operating shaft referenced 498 coaxially slidingly disposed within tubular mounting shaft 492 and a generally cylindrical ring retaining wall referenced 497. As anastomosis ring 452 warms above the transition temperature, the memory alloy thereof enters the elastic state and expands into engagement with cylindrical retaining wall 497. Apparatus 470 is now ready for use.

After inserting apparatus 460 into an organ portion (not shown) requiring excision of a diseased portion, intussusception apparatus 476 clamps a substantially mid-portion thereof (generally as disclosed hereinabove in relation to FIGS. 16–18) causing intussusception thereof. Following intussusception, mounting member 486 and applicator member 496 are aligned with recess 456 of crimping support element 454. With mounting member 486 fixed in this position, applicator member 496 is distally advanced, thereby releasing anastomosis ring 452 therefrom, to expand so as to bring organ walls (not shown) into crimping engagement against crimping support element 454. Excision of the intussuscepted organ portion is then carried out (generally as disclosed hereinabove in relation to FIGS. 18–20). Thereafter, withdrawing apparatus 460 from the anastomosed hollow organ causes crimping support element 454 together with anastomosis ring 452 to become detached from mounting projections 474 of apparatus 460.

The consequence of utilizing apparatus 460 together with intratubular expandable anastomosis ring 452 and external crimping support element 454 is the provision of a generally larger aperture formed within the organ at the site of anastomosis, compared with that formed when using an internal crimping support member. Nevertheless, the aperture is limited by the wall thickness and external diameter of external crimping support element 454. External crimping support element 454 is selected in accordance with the internal diameter of the organ to be treated. Inevitably, an aperture formed at the site of the anastomosis is smaller than the original organ diameter. In order to further increase the anastomosed aperture, in accordance with further embodiments of the present invention, an expandable crimping support element and apparatus for utilizing this expandable crimping support element is disclosed hereinbelow in relation to FIGS. 26–31. Following crimping the organ walls using an expandable anastomosis ring against an expandable crimping support element, the aperture formed at the site of anastomosis will be in accordance with the expanded size of the expandable crimping support element.

Figure 26:
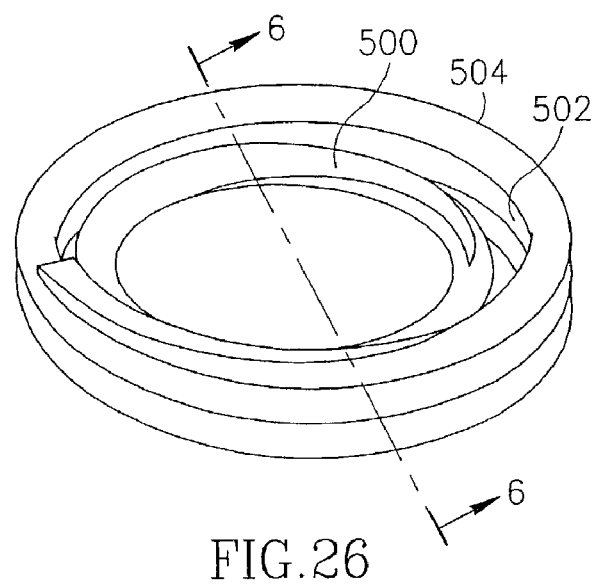
FIG. 26 illustrates a perspective view of an expandable anastomosis ring in crimping engagement with an expandable helix crimping support element in accordance with an alternative embodiment of the present invention.
Figure 27:
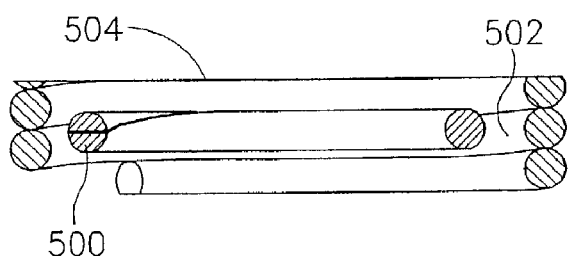
FIG. 27 illustrates a cross-sectional view of the expandable anastomosis ring and expandable helix crimping support element as shown in FIG. 26.
Figure 28:
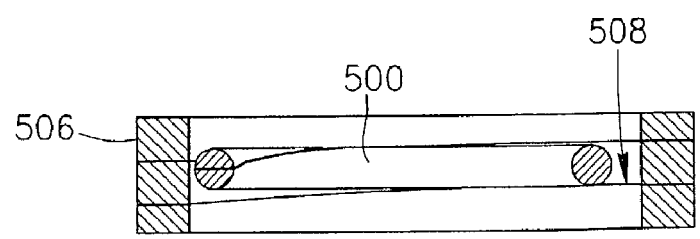
FIG. 28 illustrates a cross-sectional view of the expandable anastomosis ring and an expandable helix crimping support element formed from square section wire generally as shown in FIG. 26.

Referring now to FIGS. 26–28, there is seen an expandable anastomosis ring referenced 500 in crimping engagement with an organ portion (not shown) against an inner face referenced 502 of an expandable helical crimping support element referenced 504 configured from a length of substantially circular cross-section memory alloy wire, in accordance with an alternative embodiment of the present invention. In FIG. 27 there is seen a cross-section of expandable anastomosis ring 500 and expandable helical crimping support element 504 taken along line 6—6 in FIG. 26. In FIG. 28 there is seen a cross-section generally as taken along line 6—6 in FIG. 26 of expandable anastomosis ring 500 and an expandable helical crimping support element referenced 506, formed from a generally square section memory alloy wire, thereby forming a generally flatter inner face referenced 508.

Figure 29:
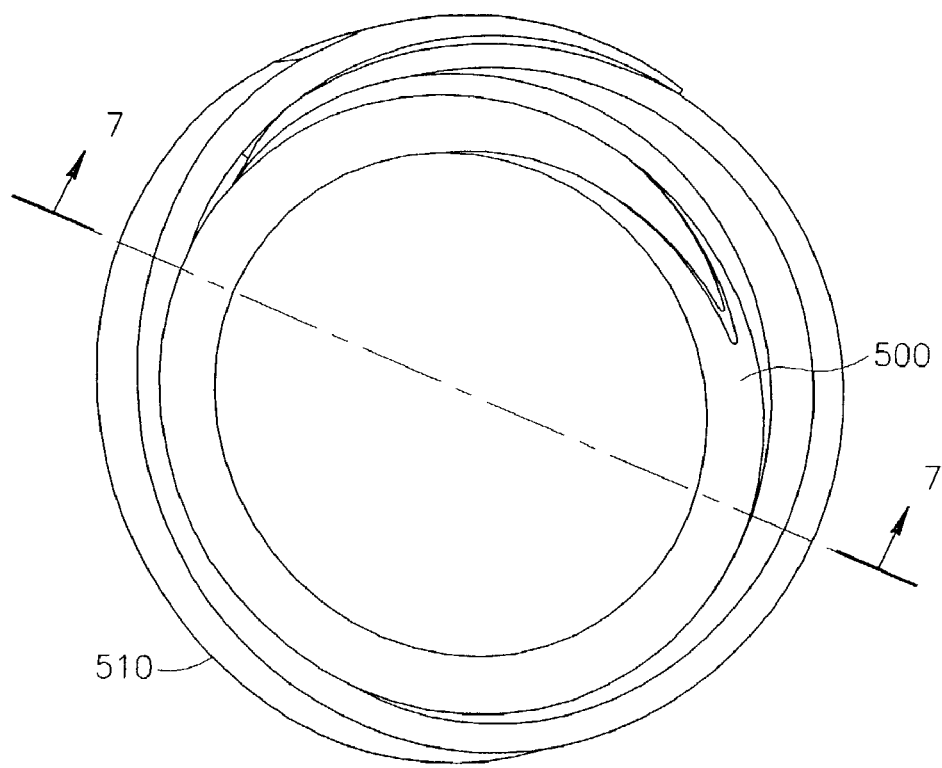
FIG. 29 illustrates a perspective view of an expandable anastomosis ring in crimping engagement with an expandable coiled flat section crimping support element in accordance with another embodiment of the present invention.
Figure 30:
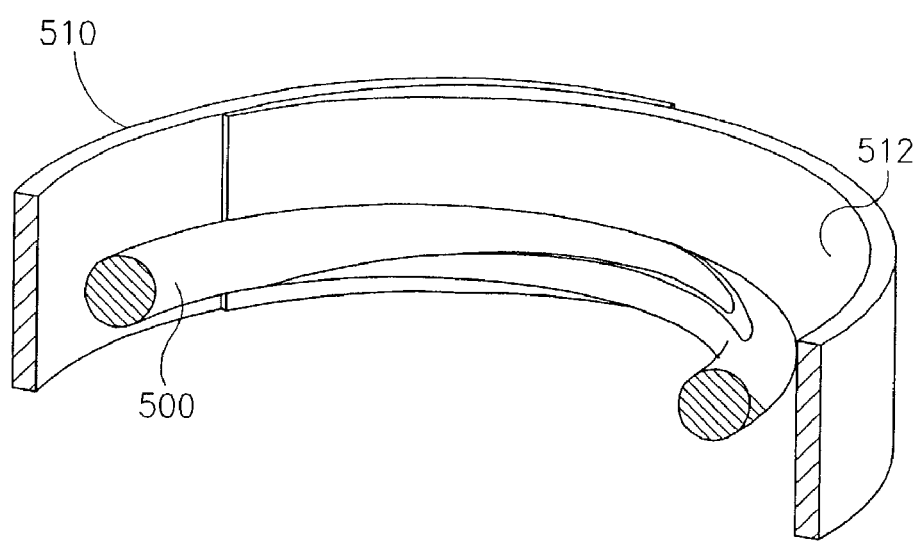
FIG. 30 illustrates a perspective cross-sectional view of the expandable anastomosis ring in crimping engagement with the coiled flat section crimping support element as shown in FIG. 29.

Referring now to FIGS. 29 and 30, in accordance with a variation of an embodiment of the present invention, there is seen expandable anastomosis ring 500 in crimping engagement with organ portions (not shown) against a substantially single coil expandable crimping support element referenced 510. FIG. 30 is a cross-section taken along line 7—7 of FIG. 29. Expandable crimping support element 510 is formed from a substantially flat section strip of memory alloy, having a generally cylindrical configuration and having a generally smooth internal surface referenced 512.

Figure 31:
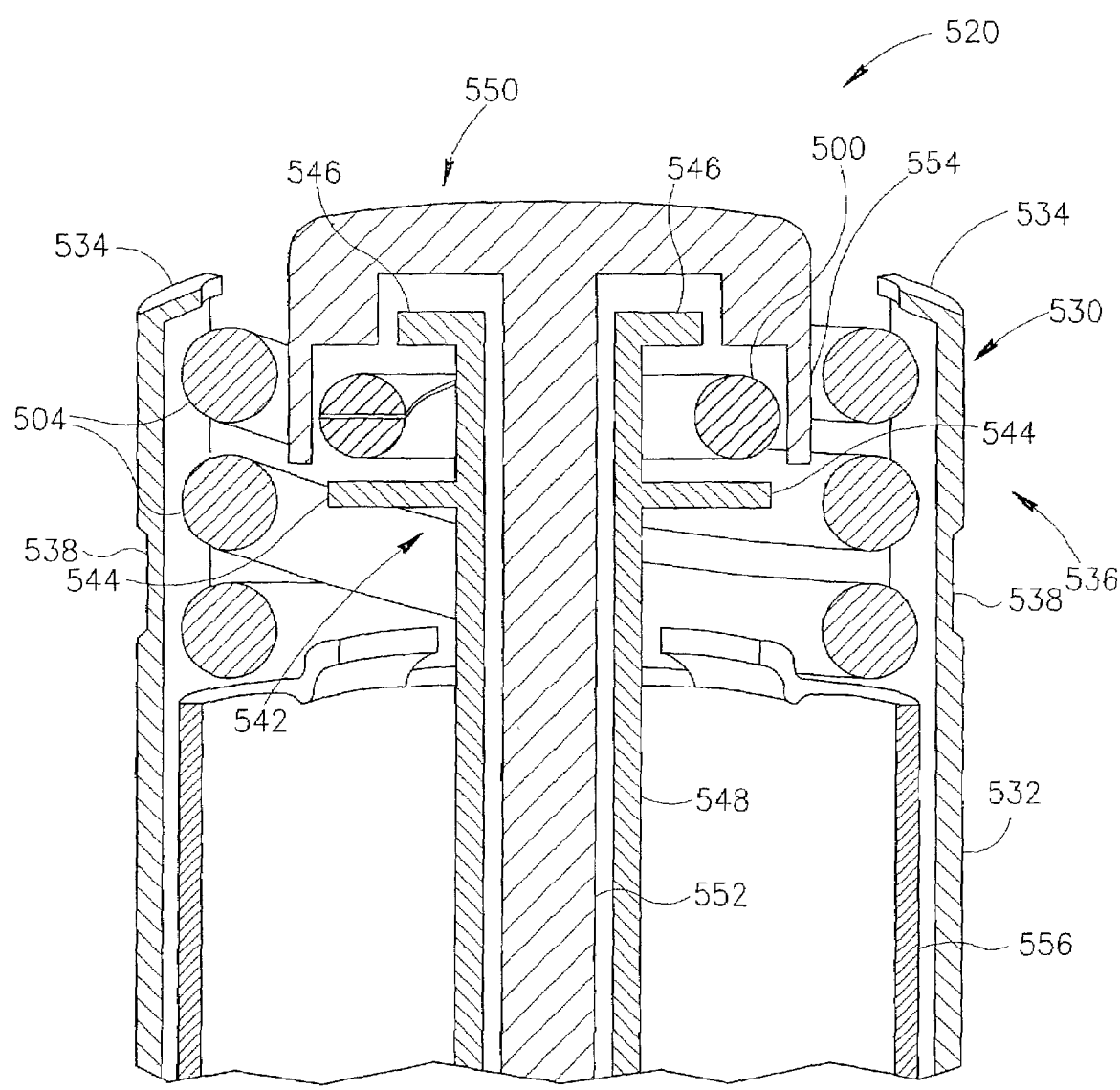
FIG. 31 illustrates an anastomosis mechanism for applying the expandable anastomosis ring and the expandable helix crimping support element as shown in FIGS. 26 to 30.

Referring now to FIG. 31, there is seen an intussusception and anastomosis apparatus, generally referenced 520 including anastomosis apparatus generally referenced 530 for causing anastomosis of portions of a hollow organ (not shown) by bringing an intratubular expandable anastomosis ring 500 into crimping engagement with intussuscepted organ wall portions (not shown) against external expandable crimping support element 504 (as disclosed hereinabove in relation to in FIGS. 26–30).

Crimping support element 504 is cooled below the transition temperature so that the memory alloy thereof becomes malleable thereby allowing crimping support element 504 to become compressible for insertion within retaining collets referenced 534 formed at a distal end 536 of enclosure 532. Collets 534 are rendered outwardly flexible as a result of recesses referenced 538 formed in an outer face thereof.

Coaxially disposed within cylindrical enclosure 532 is an intussusception apparatus (not shown; generally as disclosed in relation to FIG. 25). Further, coaxially disposed within enclosure 532 there is anastomosis apparatus 530 including an anastomosis ring mounting member referenced generally 542, which includes proximal and distal anastomosis ring holders respectively referenced 544 and 546, axially operable by a coaxial slidingly operable tubular mounting shaft referenced 548.

In order to position expandable anastomosis ring 500 between holders 544 and 546 as indicated, anastomosis ring 500 is cooled to or below the transition temperature so as to become expandably malleable. To prevent expandable anastomosis ring 500 from expanding away from mounting member 542, there is a coaxial anastomosis ring applicator member generally referenced 550 having an applicator operating shaft referenced 552 coaxially slidingly disposed within tubular mounting shaft 548. Applicator member 550 further has a generally cylindrical anastomosis ring retaining wall referenced 554. As anastomosis ring 500, positioned in mounting member 542, warms above the transition temperature, the memory alloy thereof enters the elastic state and expands into engagement with cylindrical retaining wall 554. Apparatus 520 is now ready for use.

After inserting apparatus 520 into an organ (not shown) requiring excision of a diseased portion, intussusception apparatus (not shown) causes intussusception of the diseased organ portion (generally as disclosed hereinabove in relation to FIGS. 16–18). Following intussusception, mounting member 542 and applicator member 550 are generally centrally aligned with crimping support element 504. With mounting member 542 fixed in this position, applicator member 550 is distally advanced, thereby releasing anastomosis ring 500 therefrom, to expand so as to bring organ walls (not shown) into crimping engagement against crimping support element 504. Excision of the intussuscepted organ portion is carried out (generally as disclosed hereinabove in relation to FIGS. 18–20). Thereafter, disengaging member referenced 556 is distally advanced causing crimping support element 504 together with anastomosis ring 500 to push against and thereby to force collets 534 to flex outwards at recesses 538. Crimping support element 504 together with anastomosis ring 500 is thereby detached from apparatus 520 and both crimping support element 504 and anastomosis ring 500 expand further to a preselected size.

Utilizing apparatus 520 together with intratubular expandable anastomosis ring 500 and one of external expandable crimping support elements 504, 506 or 510 (FIGS. 26–30), a generally larger aperture is formed within the organ at the site of anastomosis, which is not limited by the wire thickness and diameter of external crimping support elements 504, 506 or 510. Rather, in accordance with further embodiments of the present invention, the anastomosed aperture is formed in accordance with the expanded diameters of anastomosis ring 500 and of expandable crimping support elements 504, 506 or 510.

Figure 32:
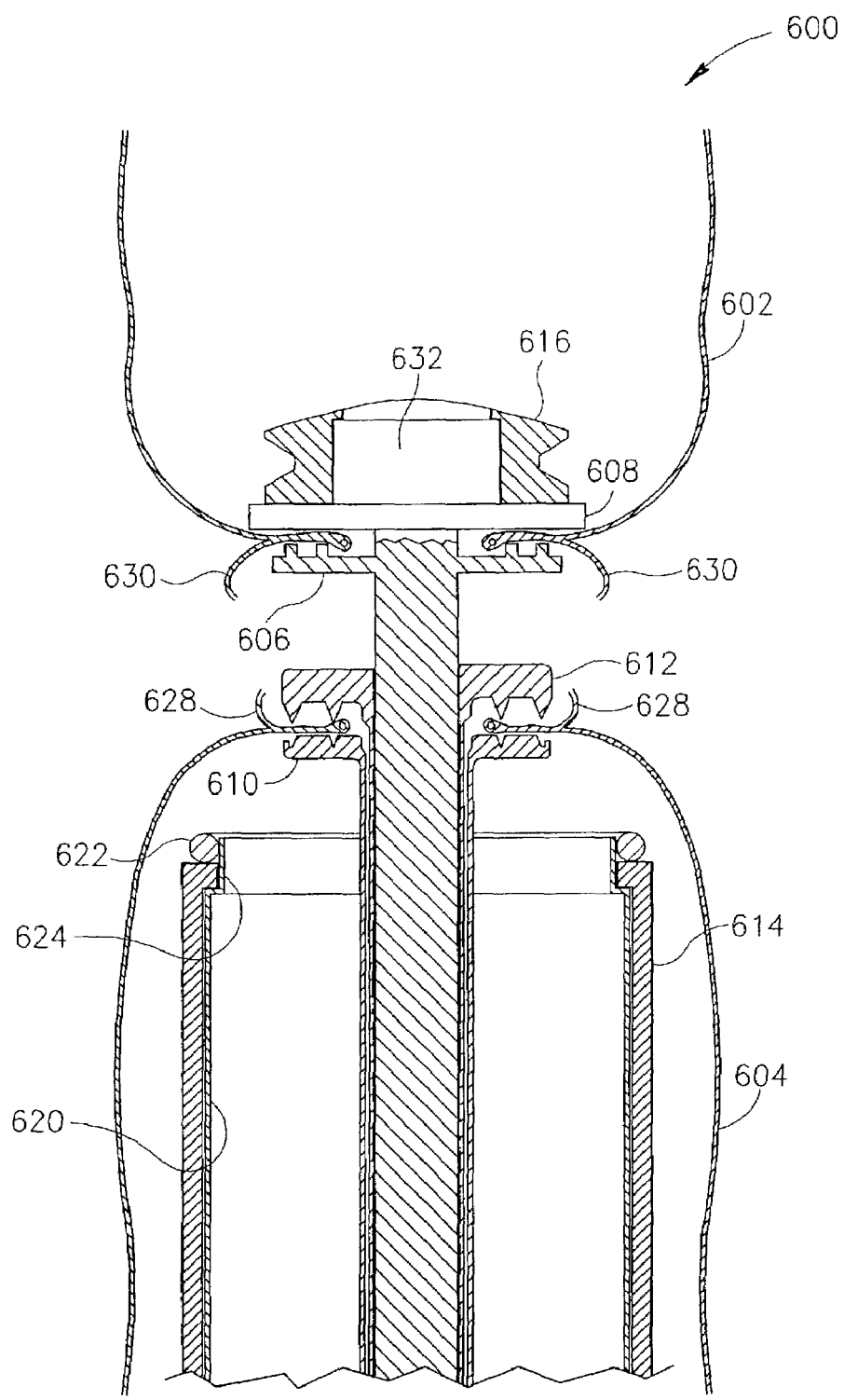
FIG. 32 illustrates surgically excised bowel portions clamped prior to anastomosis in accordance with an alternative embodiment of the present invention.

Under certain circumstances, the surgeon may decide to carry out a conventional, open surgery excising procedure in order to excise a portion of diseased or problematic bowel. The conventional method of joining the bowel portions is utilizing staples or sutures. However, according to an alternative embodiment of the present invention, using an anastomosis ring and a crimping support element, anastomosis is achieved whereby the risk of leakage is substantially reduced and no staples or sutures remain in the anastomosed bowel. Referring now to FIG. 32, there is seen a modified intussusception and anastomosis apparatus generally referenced 600, inserted into organ portion referenced 604, clamping surgically excised bowel portions referenced 602 and 604. The intussusception and anastomosis apparatus (as disclosed hereinabove in relation to FIGS. 11–12), is modified, in so fir as an additional clamping jaw referenced 606 is disposed immediately proximate to transverse crimping support applicator 608 to facilitate clamping surgically excised organ portion 602 therebetween. Organ portion 604 is clamped between jaws referenced 610 and 612.

Figure 33:
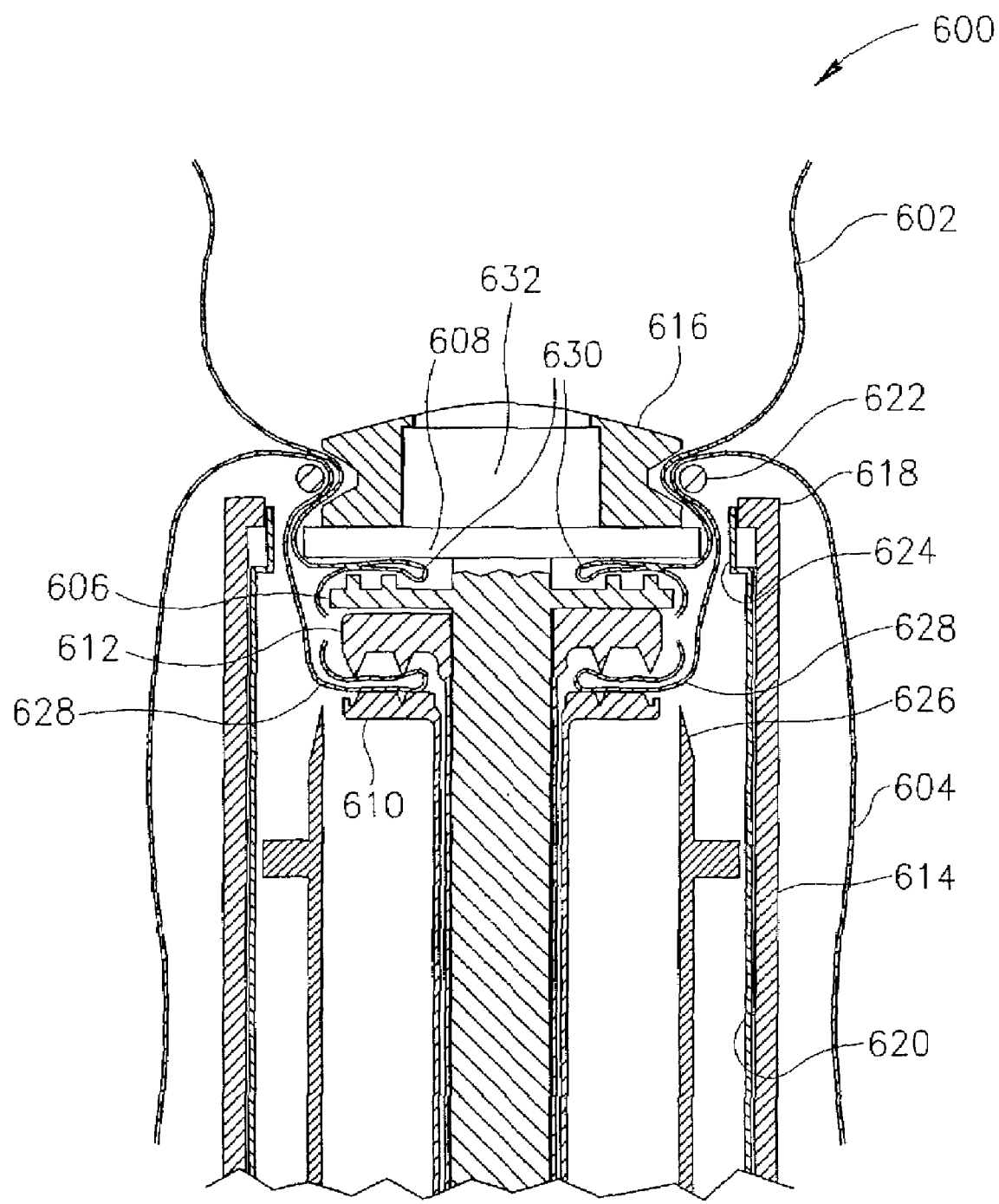
FIG. 33 illustrates crimped surgically excised bowel portions with a cylindrical cutting blade positioned prior to cutting engagement therewith.

Referring now to FIG. 33, clamped organ portions 602 and 604 are partially intussuscepted by simultaneously retracting clamping jaws 610 and 612 in clamping engagement with organ portion 604 into enclosure 614 and thereafter simultaneously retracting transverse crimping support applicator 608 and clamping jaw 606 in clamping engagement with organ portion 602. Both pairs of clamps, 606 and 608 and 610 and 612 are further retracted to cause crimping support element 616 to be aligned with lip 618 of enclosure 614. Anastomosis ring applicator referenced 620 is then retracted so as to release anastomosis ring 622 from recess referenced 624 thereby to crimp organ portions 602 and 604 against crimping support element 616. Cylindrical cutting blade referenced 626 is distally advanced to provide cutting engagement with crimped organ portions 602 and 604 and to excise clamped portions referenced 628 and 630 therefrom. Thereafter, crimping support element 616 and anastomosis ring 622 arc disengaged from crimping support applicator referenced 632 (as disclosed hereinabove in relation to FIGS. 21–23) to provide patency to anastomosed organ portions 602 and 604.

Figure 34:
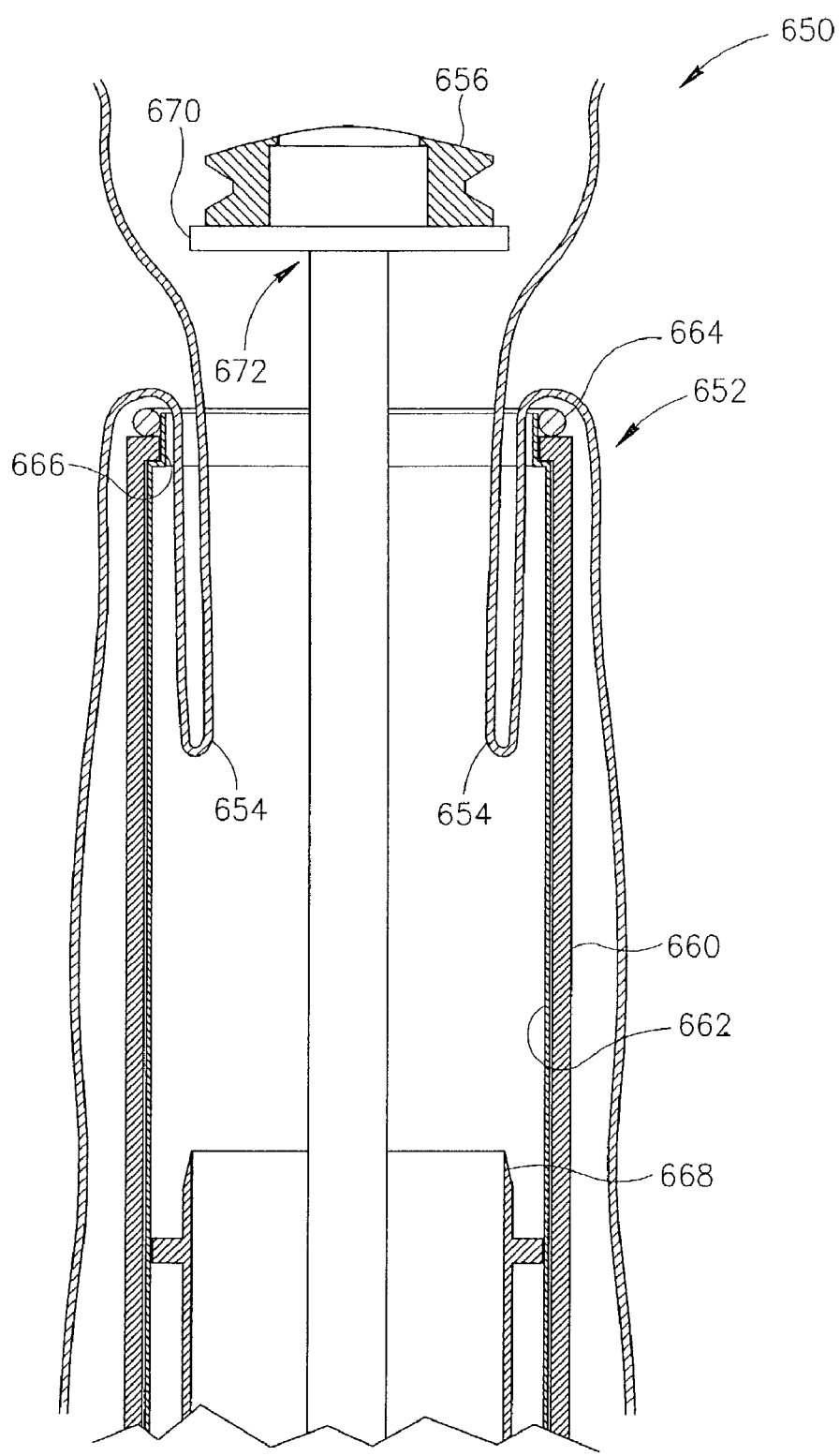
FIG. 34 illustrates a partial cross-sectional view of apparatus inserted into a prolapsed bowel for anastomosis.
Figure 35:
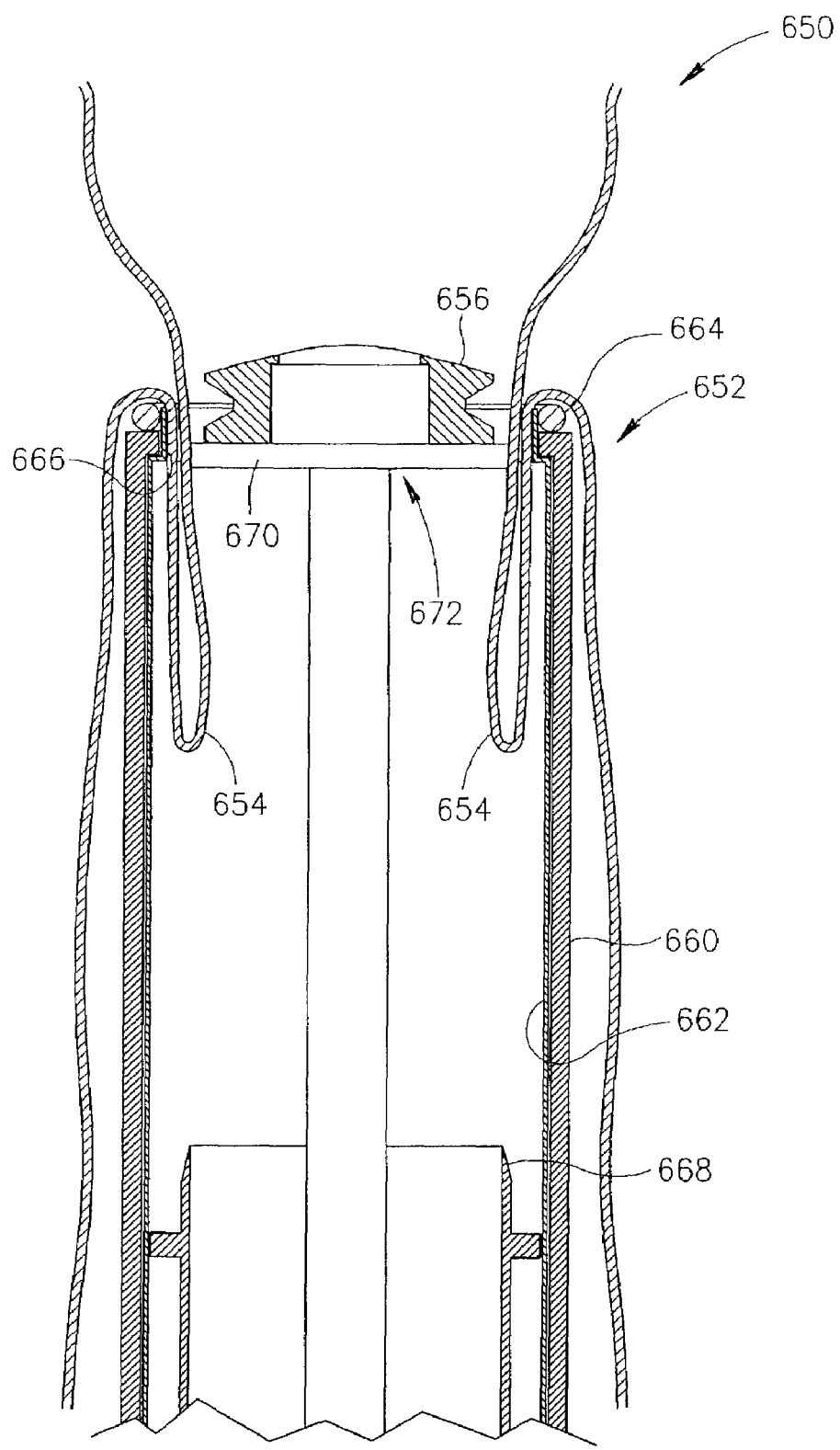
FIG. 35 illustrates a cross-sectional view of a crimping support element positioned prior to crimping of a prolapsed bowel.
Figure 36:
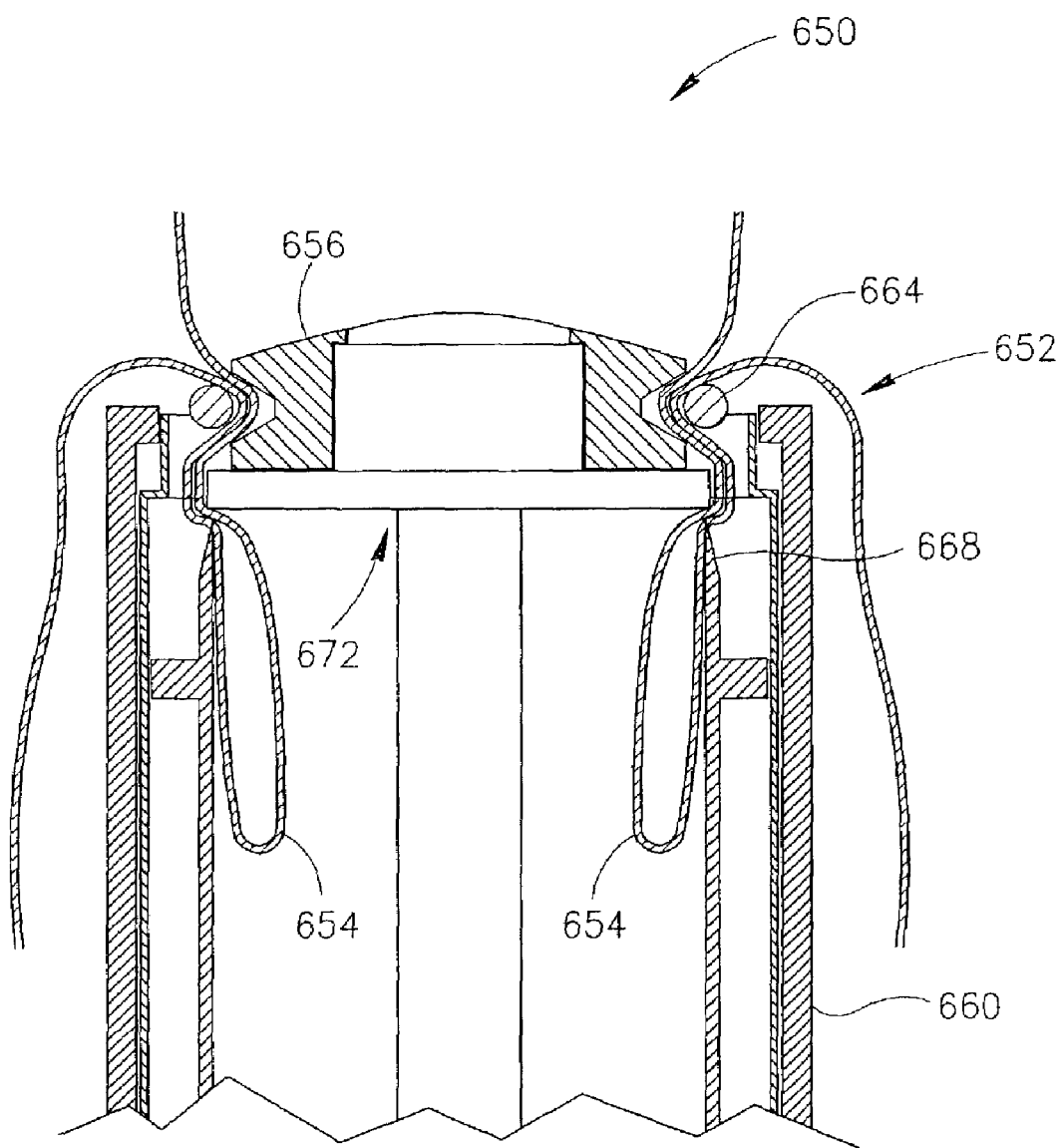
FIG. 36 illustrates anastomosis of a prolapsed bowel with a cylindrical cutting blade in cutting engagement therewith.

Referring now to FIGS. 34, 35 and 36, in accordance with a further embodiment of the present invention, there is seen an intratubular anastomosis apparatus generally referenced 650 inserted into a prolapsed bowel generally referenced 652 for bringing about anastomosis of organ 652 followed by excising of prolapsed portion referenced 654. In FIG. 35 there is seen crimping support element referenced 656 proximally retracted to be brought into alignment with recess referenced 666 of crimping support element 656 in preparation for crimping prolapsed bowel portion 654 against crimping support element 656. Retraction of anastomosis ring applicator referenced 662, causes anastomosis ring referenced 664 to disengage from recess 666 and to crimp prolapsed organ portion 654 as seen in FIG. 36. Thereafter, cylindrical cutting blade referenced 668 is brought into cutting engagement with crimping support applicator referenced 672 thereby to excise prolapsed organ portion 654. Crimping support element 656 and anastomosis ring 664 are disengaged from crimping support applicator 672 (as disclosed hereinabove in relation to FIGS. 21–23) to provide patency to anastomosed organ 652.

Figure 37:
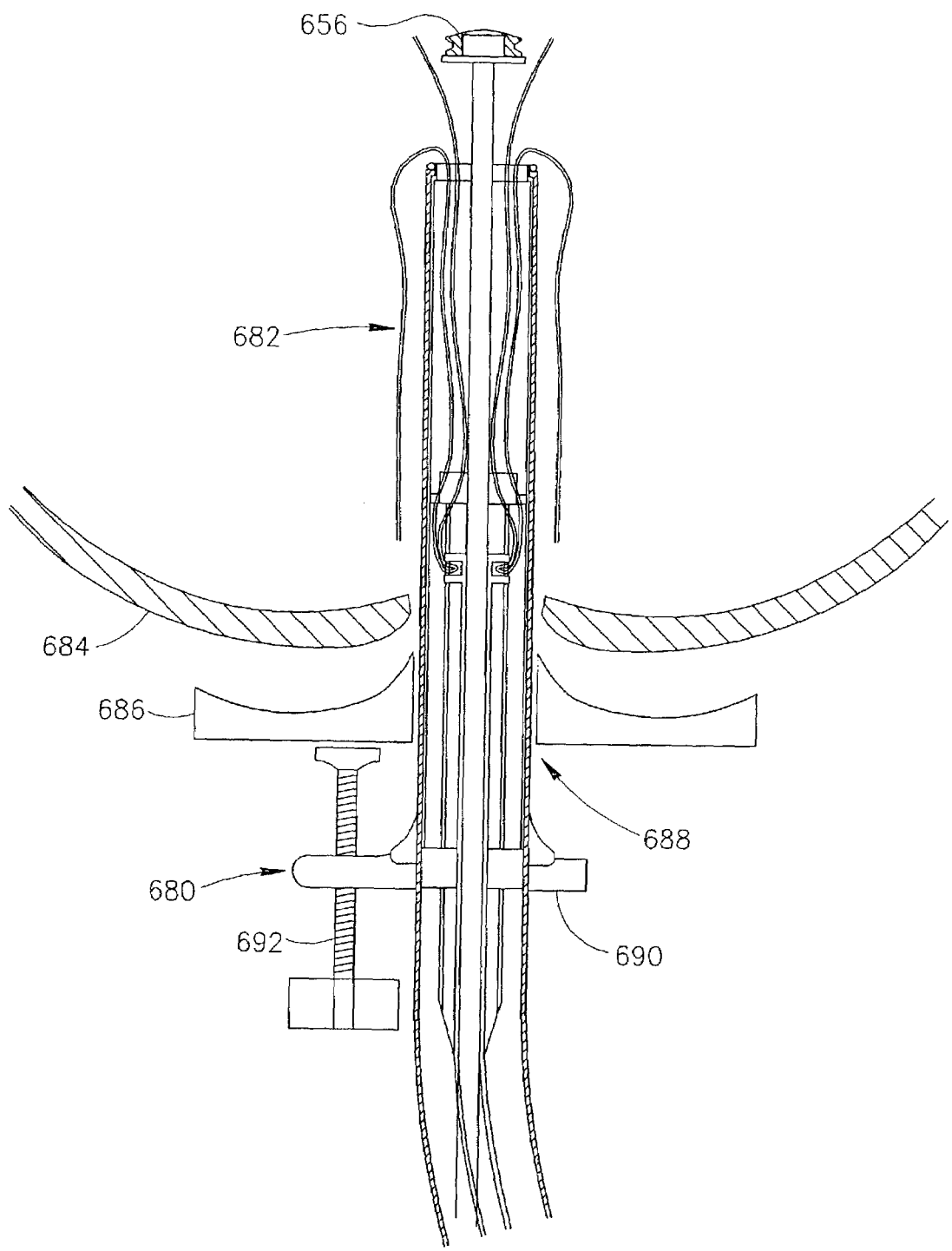
FIG. 37 illustrates a schematic view of an apparatus to provide controlled retraction of intussusception and anastomosis apparatus.

Referring now to FIG. 37, there is seen an apparatus generally referenced 680 to provide controlled positioning and retraction of intussusception and anastomosis apparatus referenced generally 682 in relation to the buttocks wall referenced 684 of a patient. A curved positioning plate referenced 686 having a generally central opening referenced 688 is placed against the buttocks of the patient. Clamp referenced 690 is fixably attached to apparatus 682 at a preselected position. Apparatus 680 is inserted through opening 688 into the anus and into the patient's rectum, where intussusception and anastomosis is to be carried out. Adjusting screw referenced 692 provides means for adjusting the position of apparatus 682 within the patient. Also, retraction of apparatus 682 is carried out by means of screw 692.

Figure 38:
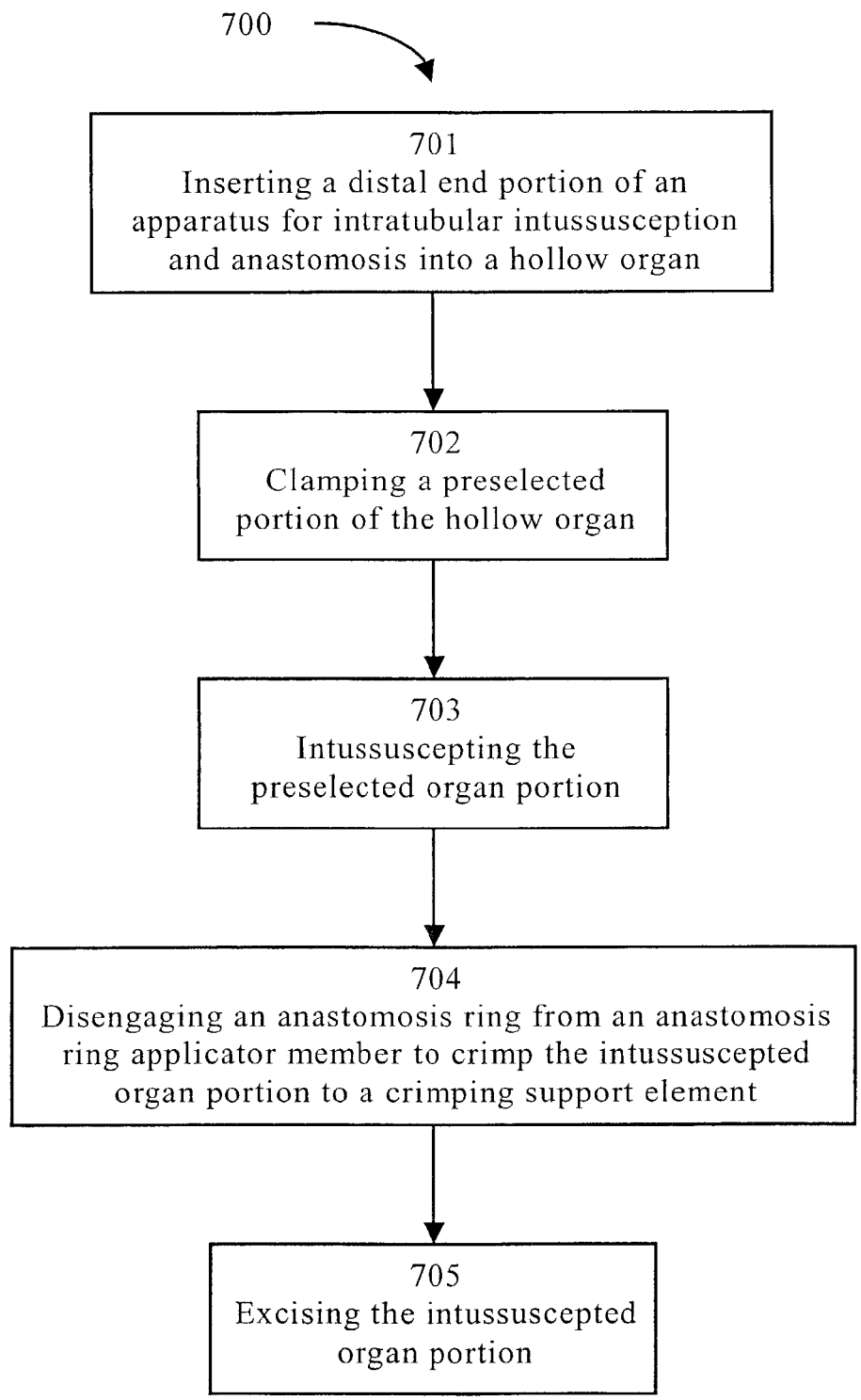
FIG. 38 illustrates a schematic representation of the method steps in accordance with a preferred embodiment of the present invention.

Referring now to FIG. 38, there is seen, in accordance with an embodiment of the present invention, a schematic representation of method steps generally referenced 700 relating to the present invention, namely Step 701 of inserting a distal end portion of an apparatus for intratubular intussusception and anastomosis a preselected distance into a hollow organ;

Step 702 of clamping a preselected portion of the hollow organ utilizing a clamping means of the intussusception and anastomosis apparatus;

Step 703 of intussuscepting the preselected organ portion by withdrawing the clamping means a preselected distance into an enclosure member;

Step 704 of disengaging an anastomosis ring from an anastomosis ring applicator member so as to crimp the intussuscepted organ portion to a crimping support element; and Step 705 of excising the intussuscepted organ portion.

In accordance with other embodiments of the present invention, step 701 of inserting includes a step of demountably engaging the anastomosis ring formed of a shape memory alloy to the anastomosis ring applicator member. Also, the step of demountably engaging includes a step of cooling the anastomosis ring below a transition temperature so as to assume a plastic state. Further, step 702 of clamping a preselected portion of the hollow organ includes a step of drawing a substantially middle portion of the preselected organ portion within the clamping means.

Figure 39:
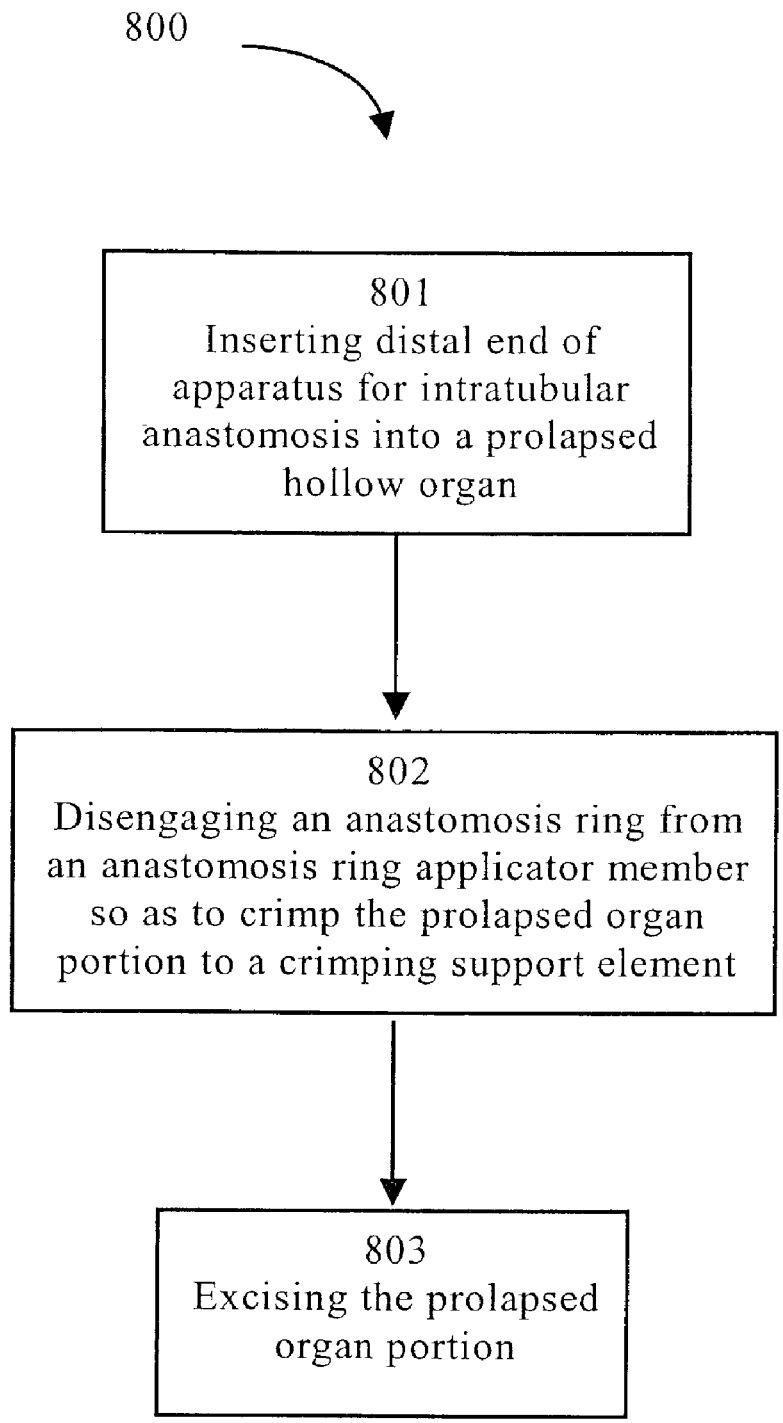
FIG. 39 illustrates a schematic representation of the method steps relating to a prolapsed bowel in accordance with an alternative embodiment of the present invention.

Referring now to FIG. 39, there is seen a schematic representation of method steps referenced generally 800 relating to a prolapsed bowel in accordance with an alternative embodiment of the present invention, namely Step 801 of inserting a distal end portion of an apparatus for intratubular intussusception and anastomosis a preselected distance into a hollow organ so as to juxtapose a crimping support element and an anastomosis ring to the prolapsed organ portion;

Step 802 of disengaging the anastomosis ring from an anastomosis ring applicator member so as to crimp the prolapsed organ portion against the crimping support element; and Step 803 of excising the prolapsed organ portion.

It will, further, be appreciated by persons skilled in the art that there is a direct relationship between the size and thickness of the anastomosis ring and crimping support element used in the surgical procedure disclosed above and the size and shape of the organ to be treated. An anastomosis ring and crimping support element of a particular size is selected so as to achieve an aperture of a requisite size as appropriate to the situation and the hollow organ to be subjected to intussusception and anastomosis. Clearly, a smaller size is appropriate for use in the upper bowel and a larger size in the lower bowel.

Additionally, it will be appreciated by persons skilled in the art, that an apparatus employing a shape memory alloy, such as an anastomosis ring, referred to hereinabove according to embodiments of the present invention, may be described as being of one of two different types. A first type of apparatus employs a shape memory alloy, which is in an easily deformable, martensitic state when it is cooled to below room temperature, called a "Cold" type. This first apparatus achieves a fully or partially austenitic state at room temperature, and a completely austenitic state when heated to at least its upper phase transition temperature, between room and body temperature. In a second type of apparatus, the shape memory alloy is in an easily deformable, martensitic state at room temperature, called a "Hot" type, whereat the apparatus is deformed and applied, and the shape memory alloy achieves a completely austenitic state when heated to above room temperature. The temperature range over which the shape memory alloy is easily deformable defines the difference between the two types of apparatus. Thus, utilizing an apparatus including a shape memory alloy of the second Hot type allows more freedom in application without necessitating cooling below room temperature. The present invention disclosed hereinabove relates to an apparatus of the first Cold type, necessitating cooling below room temperature.

Considering the "Hot" type, in which the transformation temperature is higher, the clip is martensitic at room temperature and heated to about 42–45° C. to assume an austenitic state. When the temperature drops to 37° C., that is, body temperature, the martensitic transformation is not complete, leaving the clip in a transition state, with inferior mechanical characteristics.

It should be understand that the so-called transformation temperature of the alloy, in fact, is a process of transformation. Transition from a martensitic to an austenitic state starts at a temperature $A_s$ and ends with a temperature $A_f$ at which the state becomes fully austenitic. When transforming from austenitic to martensitic state, by dropping the temperature, the alloy starts to become martensitic at temperature $M_s$, and reaches a full martensitic state at temperature $M_f$.

In the Cold type, generally preferred in accordance with embodiments of the present invention, $A_f$ is lower than body temperature, generally about 25° C. In the Hot type, $M_f$ is below body temperature, so that the alloy does not become fully martensitic at body temperature.

It will be appreciated by persons skilled in the art that the present invention is not limited by the drawings and description hereinabove presented. Rather, the invention is defined solely by the claims that follow.

What is claimed is:

1. An intratubular anastomosis apparatus for joining organ wall portions of a hollow organ after intussusception, said apparatus including:
   a) an anastomosis ring, including a length of a wire formed of a shape memory alloy defining a closed generally circular shape, having a central opening, and having overlapping end portions, said anastomosis ring for crimping adjacent intussuscepted organ wall portions against a crimping support element so as to cause anastomosis therebetween,
   wherein, said anastomosis ring and said shape memory alloy assumes
      i) a plastic or malleable state, when at a first, lower temperature; and
      ii) an elastic state, when reaching at least a second, higher temperature,
   thereby enabling said anastomosis ring to retain a preselected configuration at the first, lower temperature, and an elastic crimping configuration upon reverting to the second, higher temperature; and
   b) said crimping support element for intratubular insertion so as to provide a support for crimping said organ wall portions against said support element, said crimping support element having:
      i) a generally cylindrical side-wall;
      ii) proximal and distal end walls formed generally transversely to said side-wall, thereby to define therewith said crimping support element;
      iii) a generally axial aperture for providing flow communication therethrough; and
      iv) an attachment means for operationally engaging said crimping support element to a crimping applicator member so as to position said crimping support element adjacent to said anastomosis ring for facilitating crimping of preselected wall portions of a hollow organ therebetween.

2. An intratubular anastomosis apparatus according to claim 1, wherein said length of wire is formed having a cross-sectional shape substantially as selected from the group including:
   a) circular; and
   b) elliptical,
   thereby to control pressure applied to tissue compressed between said anastomosis ring and said crimping support element.

3. An intratubular anastomosis apparatus according to claim 1, wherein said anastomosis ring is a contracting anastomosis ring at the second higher temperature.

4. An intratubular anastomosis apparatus according to claim 3, wherein said crimping support element has an circumferential recess formed in an outer surface thereof for facilitating retaining said contracting anastomosis ring in a predetermined position therein.

5. An intratubular anastomosis apparatus according to claim 1, wherein said anastomosis ring is an expanding anastomosis ring at the second higher temperature.

6. An intratubular anastomosis apparatus according to claim 5, wherein said crimping support element has an circumferential recess formed in an inner surface thereof for facilitating retaining said expanding anastomosis ring in a predetermined position therein.

7. An intratubular anastomosis apparatus according to claim 1, wherein said crimping support element is configured as a crimping support helix including at least one coil formed of a shape memory alloy such that said crimping support helix is an expanding support helix at the second higher temperature.

8. Apparatus for intratubular intussusception and anastomosis of a preselected wall portion of a hollow organ, said apparatus including:
   a) a generally cylindrical enclosure member having a proximal and a distal end;
   b) an intratubular intussusception device, generally coaxially disposed within said enclosure member, for intussusception of a preselected hollow organ portion to be excised from the hollow organ, said intussusception device including:
      i) clamping means disposed at a distal end of said device; and
      ii) activating means, operationally connected to said clamping means, disposed at a proximal end of said device;
   c) an intratubular anastomosis apparatus disposed within said enclosure member for joining the wall portions of the hollow organ after intussusception, said anastomosis apparatus including:
      i) an anastomosis ring, including a length of a wire formed of a shape memory alloy defining a closed generally circular shape, having a central opening, and having overlapping end portions, said anastomosis ring for crimping adjacent intussuscepted organ wall portions against a crimping support element so as to cause anastomosis therebetween,
      wherein, said anastomosis ring and said shape memory alloy assumes
         (1) a plastic state, when at a first, lower temperature; and
         (2) an elastic state, when reaching at least a second, higher temperature,
      thereby enabling said anastomosis ring to retain a preselected configuration at the first, lower temperature, and an elastic crimping configuration upon reverting to the second, higher temperature; and
      ii) said crimping support element for intratubular insertion so as to provide a support for crimping said organ wall portions against said support element, said crimping support element having:
         (1) a generally cylindrical side-wall;
         (2) proximal and distal end walls arranged generally transversely to said side-wall, thereby to define therewith said crimping support element;
         (3) a generally axial aperture for providing flow communication therethrough; and
         (4) an attachment means for operationally engaging said crimping support element to a crimping support element applicator member so as to position said crimping support element adjacent to said anastomosis ring; and
   d) a surgical excising means, for excising the preselected intussuscepted hollow organ portion, said excising means operatively associated with said intratubular anastomosis apparatus, selectably operable, after crimping adjacent intussuscepted organ wall portions against said crimping support element with said anastomosis ring.

9. Apparatus for intratubular intussusception and anastomosis according to claim 8, wherein said clamping means includes a coaxial pair of jaw elements having a generally disc-like configuration operatively disposed to move relative to each other and to said apparatus.

10. Apparatus for intratubular intussusception and anastomosis according to claim 8, wherein said activating means, operationally connected to said clamping means, is remotely disposed therefrom.

11. Apparatus for intratubular intussusception and anastomosis according to claim 8, wherein said surgical excising means includes a generally cylindrical cutting blade member operative axially.

12. Apparatus for intratubular intussusception and anastomosis according to claim 8, wherein said surgical excising means is operatively associated with an excising controller remotely disposed therefrom.

13. Apparatus for intratubular intussusception and anastomosis according to claim 8, wherein said apparatus includes an optical device, said optical device affixed to said apparatus, for permitting viewing of the organ being intussuscepted and anastomosed.

14. A method for intratubular intussusception and anastomosis of a hollow organ wall portion, said method includes:
  a) inserting a distal end portion of an apparatus for intratubular intussusception and anastomosis a preselected distance into a hollow organ;
  b) clamping a preselected portion of the hollow organ utilizing a clamping means of the intussusception and anastomosis apparatus;
  c) intussuscepting the preselected organ portion by withdrawing the clamping means a preselected distance into an enclosure member;
  d) disengaging an anastomosis ring from an anastomosis ring applicator member so as to crimp the intussuscepted organ portion against a crimping support element; and
  e) excising the intussuscepted organ portion,
  wherein said step of inserting includes a step of demountably engaging the anastomosis ring formed of a shape memory alloy to the anastomosis ring applicator member.

15. The method according to claim 14, wherein said step of demountably engaging includes a step of cooling the anastomosis ring below a first transition temperature so as to assume a plastic state thereof.

16. A method for intratubular intussusception and anastomosis of a hollow organ wall portion, said method includes:
  a) inserting a distal end portion of an apparatus for intratubular intussusception and anastomosis a preselected distance into a hollow organ;
  b) clamping a preselected portion of the hollow organ utilizing a clamping means of the intussusception and anastomosis apparatus;
  c) intussuscepting the preselected organ portion by withdrawing the clamping means a preselected distance into an enclosure member;
  d) disengaging an anastomosis ring from an anastomosis ring applicator member so as to crimp the intussuscepted organ portion against a crimping support element; and
  e) excising the intussuscepted organ portion,
  wherein said step of clamping a preselected portion of the hollow organ includes a step of drawing a substantially middle portion of the preselected organ portion within the clamping means.

* * * * *